United States Patent
Yu et al.

(10) Patent No.: US 11,060,083 B2
(45) Date of Patent: *Jul. 13, 2021

(54) METHODS AND COMPOSITIONS FOR PRODUCING DOUBLE ALLELE KNOCK OUTS

(71) Applicant: Larix Bioscience LLC, Sunnyvale, CA (US)

(72) Inventors: Bo Yu, San Jose, CA (US); James Larrick, Woodside, CA (US)

(73) Assignee: Larix Bioscience LLC, Sunnyvale, CA (US)

( * ) Notice: Subject to any disclaimer, the term of this patent is extended or adjusted under 35 U.S.C. 154(b) by 573 days.

This patent is subject to a terminal disclaimer.

(21) Appl. No.: 15/599,896

(22) Filed: May 19, 2017

(65) Prior Publication Data

US 2018/0334665 A1  Nov. 22, 2018
US 2021/0108190 A9  Apr. 15, 2021

Related U.S. Application Data

(63) Continuation of application No. 14/335,903, filed on Jul. 19, 2014, now Pat. No. 9,663,782.

(60) Provisional application No. 61/856,579, filed on Jul. 19, 2013.

(51) Int. Cl.
| | | |
|---|---|---|
| *C12N 15/67* | (2006.01) | |
| *C12N 15/79* | (2006.01) | |
| *C12N 15/113* | (2010.01) | |
| *C12N 15/10* | (2006.01) | |
| *C12N 15/90* | (2006.01) | |

(52) U.S. Cl.
CPC .......... *C12N 15/102* (2013.01); *C12N 15/113* (2013.01); *C12N 15/67* (2013.01); *C12N 15/79* (2013.01); *C12N 15/907* (2013.01); *C12N 15/1137* (2013.01); *C12N 2310/20* (2017.05); *C12Y 204/01068* (2013.01); *C12Y 302/01018* (2013.01)

(58) Field of Classification Search
None
See application file for complete search history.

(56) References Cited

U.S. PATENT DOCUMENTS

| | | | |
|---|---|---|---|
| 6,893,840 B2 | 5/2005 | Thudium et al. | |
| 6,946,292 B2 | 9/2005 | Kanda et al. | |
| 7,919,313 B2 | 4/2011 | Collingwood | |
| 8,273,723 B2 | 9/2012 | Zhang et al. | |
| 8,697,359 B1 | 4/2014 | Zhang | |
| 8,728,816 B2 | 5/2014 | Treek | |
| 8,921,332 B2 | 12/2014 | Choulika et al. | |
| 9,663,782 B2* | 5/2017 | Yu ..................... | C12N 15/102 |
| 2010/0076057 A1 | 3/2010 | Sontheimer et al. | |
| 2010/0311124 A1 | 12/2010 | Liu | |
| 2013/0311124 A1 | 11/2013 | van Bremen | |
| 2015/0024500 A1* | 1/2015 | Yu ..................... | C12N 15/102 |
| | | | 435/462 |

FOREIGN PATENT DOCUMENTS

| | | |
|---|---|---|
| CN | 101883850 | 11/2010 |
| EP | 2 527 435 | 11/2012 |
| JP | H8-510133 | 10/1996 |
| JP | 2012-507282 | 3/2012 |
| WO | WO 1994/026908 | 11/1994 |
| WO | WO 2009/009086 | 1/2009 |
| WO | WO 2013/003767 | 1/2013 |
| WO | WO 2013/098244 | 7/2013 |

OTHER PUBLICATIONS

Imai-Nishiya et al., Double knockdown of alpha-1,6-fucosyltransferase (FUT8) and GDP-mannose-4,6-dehydratase in antibody producing . . . , 2007, BMC Biotechnol. vol. 7, p. 84.
Baker, Gene editing at CRISPR speed, Apr. 2014, Nature Biotechnol. vol. 32, pp. 309-312.
Baumeister et al., A matter of cell line development, http://www.glycotope.com/wp-content/uploads/documents/Glycotope-EBR_2.pdf.
Bork et al., Increasing the sialylation of therapeutic glycoproteins: the potential of the sialic acid biosynth. pathway, 2009, J. Pharmaceut. Sci. vol. 98, pp. 3499-3508.
Burgess, A CRISPR genome-editing tool, Jan. 2013, Nature Genet. Rev. vol. 14, pp. 80-81.
Cong et al, Multiplex genome engineering using CRISPR/Cas Systems, Jan. 2013, Science vol. 339, pp. 819-823.
Conner, Beginners guide to gene targeting, 2006, MIT.
Deltcheva et al., CRISPR RNA maturation by trans-encoded small RNA and host factor RNase III, 2011, Nature vol. 471, pp. 602-607.
Duda et al., High-efficiency genome editing via 2A-coupled co-expression of . . . zinc finger nucleases or CRISPR/Cas9 nickase pairs, Apr. 2014, Nucl Acids Res. vol. 42, e84.
Esvelt et al., Genome-scale engineering for systems and synthetic biology, 2013, Molc. Sys. Biol. vol. 9, pp. 641.
Fernandes, Biopharmaceutical sialylation, 2006, Eur. Biopharmaceut. Rev. Spring 2006, pp. 100-104.
Fu et al., High-frequency off-target mutagenesis induced by CRISPR-Cas nucleases in human cells, Jun. 2013, Nature Biotechnol. vol. 31, pp. 822-826.
Gasiunas et al., Cas9-crRNA ribonucleoprotein complex mediates specific DNA cleavage for . . . immunity in bacteria, 2012, Proc. Natl Acad. Sci. vol. 109, pp. E2579-E2586.
Ghaderi et al., Production platforms for biotherapeutic glycoproteins: occurrence, impact . . . non-human sialylation, 2012, Biotech. Genet. Eng. Rev. vol. 28, pp. 147-176.

(Continued)

Primary Examiner — Channing S Mahatan
(74) Attorney, Agent, or Firm — HelixIP LLP

(57) ABSTRACT

The present invention provides a method and compositions utilizing the CRISPR system to disrupt a target gene in eukaryotic cells to produce double allele knock outs. The method finds use in producing afucosylated antibodies with enhanced ADCC activity.

19 Claims, 11 Drawing Sheets

Specification includes a Sequence Listing.

(56) References Cited

OTHER PUBLICATIONS

Goncalves et al., Concerted nicking of donor and chromosomal acceptor DNA promotes . . . gene targeting in human cells, 2011, Nucl. Acids. Res. vol. 40, pp. 3443-3455.
Greulich et al., A platform fed-batch process fo various CEMAX producer cell lines, 2011, BMC Proceed. vol. 5(suppl), pp. P40.
Grissa et al., CRISPRFinder: a web tool to identify clustered regularly interspaced short palindromic repeats, 2007, Nucl. Acids Res. vol. 35, pp. W52-W57.
Herbst et al., B-cell depletion in vitro and in vivo with an afucosylated anti-CD19 antibody, 2010, J. Pharmacol. Expt. Therapeut. vol. 335, pp. 213-222.
Ho et al., Generation of monoclonal antibody-producing mammalian cell lines, Apr. 2013, Pharm. Bioprocess. vol. 1, pp. 71-87.
Hsu et al., DNA targeting specificity of the RNA-guided Cas9 nuclease, Jul. 21, 2013, Nature Biotechnol. Suppl. Information.
Iida et al., Two mechanisms of the enhanced antibody-dependent cellular cytotoxicity . . . in human blood, 2009, BMC Cancer vol. 9, p. 58.
Imai-Nishiya et al., Double knockdown of alpha-1,6-fucosyltransferase (FUT8) . . . with enhanced ADCC, 2007, BMC Biotechnol. vol. 7, p. 84.
Jinik et al., RNA-programmed genome editing in human cells, Jan. 2013, eLIFE vol. 2, e00471.
Jones, Performance by design: Engineering functionality into biopharmaceutical products, Jan. 2011, CHI Peptalk, San Diego CA.
Junttila et al., Superior in vivo efficacy of afucosylated trastuzumab in the treatment of HER2-amplified breast cancer, 2010, Cancer Res. vol. 70, pp. 4481-4489.
Kasermann et al., Analysis and functional consequences of increased Fab-sialylation . . . after lectin fractionation, 2012, PLos One vol. 7, p. e37243.
Kim et al., Precision genome engineering with programmable DNA-nicking enzymes, 2012, Genome Res. vol. 22, pp. 1327-1333.
Klein, Glycoengineering of therapeutic antibodies, 2012, Arzneimittelforschung vol. 62 Suppl. 1, pp. S4-S5.
Krzewinski-Recchi et al., Identification and functional expression of a second human . . . ST6Gal II, 2003, Eur. J. Biochem. vol. 270, pp. 950-961.
Lai et al., Advances in Mammalian cell line development technologies for recombinant protein production, Apr. 2013, Pharmaceut. vol. 6, pp. 579-603.
Lee et al., Alteration of terminal glycosylation sequences on N-linked oligosaccharides . . . sialyltransferase, 1989, J. Biol. Chem. vol. 264, pp. 13848-13855.
Lin et al., Blocking core fucosylation of TGF-beta 1 receptors downregulates . . . renal tubular cells, 2011, Am. J. Phsiol. Renal Physiol. vol. 300, pp. F1017-F1025.
Lin et al., Chinese Hamster Ovary (CHO) host cell engineering to increase sialylation of . . . sialyltransferase expression, 2015, Biotechnol. Prog. vol. 31, pp. 334-346.
Liu et al., ADCC enhancement technologies for next generation therapeutic antibody, Trends in Biopharmaceut. Ind. pp. 13-17.
Mali et al., RNA-guided human genome engineering via Cas9, Jan. 2013, Science vol. 339, pp. 823-826.
Malphettes et al., Highly efficient deletion of FUT8 in CHO cell lines using zinc finger nucleases . . . antibodies, 2010, Biotechnol. Bioeng. vol. 106, pp. 774-783.
Mascarenhas et al., Improving product safety profiles: host cell lines deficient . . . alpha-1,3-galactosyltransferase(GGTA1), Sigma-Aldrich.
Masuda et al., Enhanced binding affinity for Fc-gamma-RIIIa of fucose negative antibody . . . antibody-dependent cellular cytotoxicity, 2007, Mol. Immunol. vol. 44, pp. 3122-3131.
Mori et al., Engineering chinese hamster ovary cells to maximize effector function . . . using FUT8 siRNA, 2004, Biotechnol. Bioeng. vol. 88, pp. 901-908.

Naso et al., Engineering host cell lines to reduce terminal sialylation of secreted antibodies, 2010, mAbs vol. 2, pp. 519-527.
Ngantung, Engineering mammalian cell line to improve sialylation, 2005, Ph.D. Thesis, MIT Library.
Niu et al., Generation of gene-modified cynomolgus monkey via Cas9/RNA mediated . . . embryos, Feb. 2014, Cell vol. 156, pp. 1-8.
Niwa et al., Defucosylated chimeric anti-CC chemokine receptor 4 IgG1 with enhanced . . . leukemia and lymphoma, 2004, Cancer Res. vol. 64, pp. 2127-2133.
Niwa et al., Enhanced natural killer cell binding and activation by low-fucose IgG1 . . . antigen density, 2005, Clin. Cancer Res. vol. 11, pp. 2327-2336.
Padler-Karavani et al., Potential impact of the non-human sialic acid N-glycolylneuraminic acid . . . rejection risk, 2011, Xenotransplant. vol. 18, pp. 1-5.
Park et al., CRISPR/Cas9 allows efficient and complete knock-in of a destabilization domain . . . protien function, Apr. 2014, PLos One vol. 9, p. e95101.
Pattanayak et al., High-throughput profiling of off-target DNA cleavage reveals RNA-programmed . . . specificity, Aug. 2013, Nature Biotechnol. vol. 31, pp. 839-843.
Porter et al., Antibody production by GS-CHO cell lines over extended culture periods, Lonza Poster.
Prediger, Simplifying CRISPR, Jun. 2015, OMICS Tutorial vol. 35, pp. 1-4.
Racher, Process development for monoclonal antibodies, 2004, Lonza Presentation.
Racher, Establishment of cell lines for manufacturing recombinant antibodies, 2004, Lonza Presentation.
Racher, Suitability and stability of cell lines for manufacturing antibodies: experience with GS cell lines, 2005, Lonza Presentation.
Ran et al., Double nicking by RNA-guided CRISPR Cas9 for Enhanced genome editing specificity, Sep. 2013, Cell vol. 154, pp. 1380-1389.
Raymond et al., Production of highly sialylated monoclonal antibodies, 2012, Glycosylation (ed. Petrescu) Intech, Chapter 17.
Richter et al., Function and regulation of clustered regularly interspaced short palindromic repeats . . . Systems, 2012, Viruses vol. 4, pp. 2291-2311.
Shen et al., Generation of gene-modified mice via Cas9/RNA-mediated gene targeting, May 2013, Cell Res. vol. 23, pp. 720-723.
Shields et al., Lack of fucose on human IgG1 N-linked oligosaccharide improves binding . . . Cellular Toxicity, 2002, J. Biol. Chem. vol. 277, pp. 26733-26740.
Shinkawa et al., The absence of fucose but not the presence of galactose . . . antibody-dependent cellular cytotoxicity, 2003, J. Biol. Chem. vol. 278, pp. 3466-3473.
Smith et al., Generation of a nicking enzyme that stimulates site-specific gene conversion . . . endonuclease, 2009, Proc. Natl Acad. Sci. vol. 106, pp. 5099-5104.
Sondermann et al., General mechanism for modulating immunoglobulin effector function, Jun. 2013, Proc. Natl Acad. Sci. vol. 110, pp. 9868-9872.
Stadlmann et al., Analytical and functional aspects of antibody sialylation, 2010, J. Clin. Immunol. vol. 30 (suppl), pp. S15-S19.
Suzuki et al., A nonfucosylated anti-HER2 antibody augments antibody-dependent cellular cytotoxicity . . . patients, 2007, Clin. Cancer Res. vol. 13, pp. 1875-1882.
Von Horsten et al., Production of non-fucosylated antibodies by co-expression of . . . reductase, 2010, Glycobiol. vol. 20, pp. 1607-1618.
Witzany, The agents of natural genome editing, 2011, J. Molc. Cell. Biol. vol. 3, pp. 181-189.
Cho et al., Targeted genome engineering in human cells with the Cas9 RNA-guided endonuclease, Jan. 2013, Nature Biotechnol. vol. 31, pp. 230-232.
Yamane-Ohnuki et al., Establishment of FUT8 knockout chinese hamster ovary cells . . . cellular cytotoxicity, 2004, Biotechnol. Bioeng. vol. 87, pp. 614-622.
Zhang, CRISPR: Genome Engineering Toolbox, Zhang Lab Description.
Zhou et al., One-step generation of different immunodeficient mice with multiple gene modifications by CRISPR/Cas9 . . . , Nov. 2013, Intl J. Biochem. Cell Biol. vol. 46, pp. 49-55.

(56) References Cited

OTHER PUBLICATIONS

Zhou et al., Dual sgRNAs facilitate CRISPR/Cas9 mediated mouse genome targeting, Feb. 2014, FEBS J. vol. 281, pp. 1717-1725.
Wang et al., One-step generation of mice carrying mutations in multiple genes by CRISPR/Cas-mediated genome engineering, May 9, 2013, Cell 153:910-918.
Jiang et al., CRISPR-assisted editing of bacterial genomes, Mar. 1, 2013, Nat. Biotechnol. 31:233-239.
Jinek et al., RNA-programmed editing of human cells, Jan. 23, 2013, eLife 2:e00471.
Cong et al., Multiplex genome engineering using CRISPR/Cas Systems, Feb. 15, 2013, Science 339:819-823.

* cited by examiner

CHOS WT
- LCA-FITC

CHOS WT
+ LCA-FITC

CHOS WT
(-) LCA-FITC
M2: 0.12%

CHOS WT
(+) LCA-FITC
M2: 0.17%

| m/z | Glycan code | Fucose | Rituxan WT 2-192-1 | Rituxan AF 2-192-3 | Herceptin AF 5-3-2 | Herceptin AF 5-3-3 | Herceptin WT 5-9-4 |
|---|---|---|---|---|---|---|---|
| 1241.45 | 3 3 0 0 0 | - | 0 | 0.33 | 0.57 | 0.75 | 0 |
| 1362.48 | 5 2 0 0 0 | - | 0.61 | 0.65 | 0.76 | 0.57 | 0.59 |
| 1387.51 | 3 3 1 0 0 | + | 0.19 | 0 | 0 | 0 | 0.53 |
| 1444.53 | 3 4 0 0 0 | - | 0.23 | 11.42 | 17.5 | 20.16 | 0.3 |
| 1524.53 | 6 2 0 0 0 | - | 0.15 | 0.15 | 0 | 0 | 0.18 |
| 1590.59 | 3 4 1 0 0 | + | 8.92 | 0 | 0 | 0 | 20.61 |
| 1606.59 | 4 4 0 0 0 | - | 0.12 | 2.15 | 2.87 | 0.91 | 0 |
| 1647.61 | 3 5 0 0 0 | - | - | 0.09 | 0 | 0.12 | 0 |
| 1686.59 | 7 2 0 0 0 | - | 0.09 | 0 | 0 | 0 | 0 |
| 1752.64 | 4 4 1 0 0 | + | 2.91 | 0 | 0 | 0 | 2.58 |
| 1768.64 | 5 4 0 0 0 | - | - | 0.15 | 0.18 | 0 | 0 |
| 1793.67 | 3 5 1 0 0 | + | - | 0 | 0 | 0 | 0.16 |
| 1848.64 | 8 2 0 0 0 | - | 0.08 | 0 | 0 | 0 | 0 |
| 1914.70 | 5 4 1 0 0 | + | 0.29 | 0 | 0 | 0 | 0.15 |
| 2319.81 | 5 4 1 1 0 / 4 4 2 0 1 | + | 0.09 | 0 | 0 | 0 | 0 |

SEQUENCE LISTING

```
<160> NUMBER OF SEQ ID NOS: 29

<210> SEQ ID NO 1
<211> LENGTH: 203
<212> TYPE: DNA
<213> ORGANISM: Cricetulus griseus

<400> SEQUENCE: 1
atgcgggcat ggactggttc ctggcgttgg attatgctca ttcttttttgc ctgggggacc      60 ttattgtttt ataggtgg tcatttggtt cgagataatg accaccctga ccattctagc       120
agagaactct ccaagattct tgcaaagctg gagcgcttaa aacaacaaaa tgaagacttg      180
aggagaatgg ctgagtctct ccg                                              203

<210> SEQ ID NO 2
<211> LENGTH: 205
<212> TYPE: DNA
<213> ORGANISM: Artificial Sequence
<220> FEATURE:
<223> OTHER INFORMATION: alpha 1,6 fucosyltransferase exon 1 mutant

<400> SEQUENCE: 2
atgcgggcat ggactggttc ctggcgttgg attatgctca ttcttttttgc ctgggggacc      60 ttattgtttt ataggtgg tcatttggtt cgagataatg accaccctga ccccattcta       120
gcagagaact ctccaagatt cttgcaaagc tggagcgctt aaaacaacaa aatgaagact      180
tgaggagaat ggctgagtct ctccg                                            205

<210> SEQ ID NO 3
<211> LENGTH: 202
<212> TYPE: DNA
<213> ORGANISM: Artificial Sequence
<220> FEATURE:
<223> OTHER INFORMATION: alpha 1,6 fucosyltransferase exon 1 mutant

<400> SEQUENCE: 3
atgcgggcat ggactggttc ctggcgttgg attatgctca ttcttttttgc ctgggggacc      60 ttattgtttt ataggtgg tcatttggtt cgagataatg accaccctgc cattctagca       120
gagaactctc caagattctt gcaaagctgg agcgcttaaa acaacaaaat gaagacttga      180
ggagaatggc tgagtctctc cg                                               202

<210> SEQ ID NO 4
<211> LENGTH: 111
<212> TYPE: DNA
<213> ORGANISM: Artificial Sequence
<220> FEATURE:
<223> OTHER INFORMATION: alpha 1,6 fucosyltransferase exon 1 mutant

<400> SEQUENCE: 4
atgcgggcat ggactggtcc attctagcag agaactctcc aagattcttg caaagctgga      60
gcgcttaaaa caacaaaatg aagacttgag gagaatggct gagtctctcc g               111
```

<210> SEQ ID NO 5
<211> LENGTH: 24
<212> TYPE: DNA
<213> ORGANISM: Artificial Sequence
<220> FEATURE:
<223> OTHER INFORMATION: Synthetic sequence

<400> SEQUENCE: 5
gcatggactg gttcctggcg ttgg                                  24

<210> SEQ ID NO 6
<211> LENGTH: 23
<212> TYPE: DNA
<213> ORGANISM: Artificial Sequence
<220> FEATURE:
<223> OTHER INFORMATION: Synthetic sequence

<400> SEQUENCE: 6
gttctctgct agaatggtca ggg                                   23

<210> SEQ ID NO 7
<211> LENGTH: 24
<212> TYPE: DNA
<213> ORGANISM: Artificial Sequence
<220> FEATURE:
<223> OTHER INFORMATION: Synthetic sequence

<400> SEQUENCE: 7
gctccagctt tgcaagaatc ttgg                                  24

<210> SEQ ID NO 8
<211> LENGTH: 23
<212> TYPE: DNA
<213> ORGANISM: Artificial Sequence
<220> FEATURE:
<223> OTHER INFORMATION: Synthetic sequence

<400> SEQUENCE: 8
ggagaatggc tgagtctctc cgg                                   23

<210> SEQ ID NO 9
<211> LENGTH: 27
<212> TYPE: DNA
<213> ORGANISM: Artificial Sequence
<220> FEATURE:
<223> OTHER INFORMATION: Synthetic sequence

<400> SEQUENCE: 9
gaataccaga aggccctatt gatcagg                               27

<210> SEQ ID NO 10
<211> LENGTH: 24
<212> TYPE: DNA
<213> ORGANISM: Artificial Sequence
<220> FEATURE:
<223> OTHER INFORMATION: Synthetic sequence

<400> SEQUENCE: 10
gaagaaatta agaaattag aagg                                   24

<210> SEQ ID NO 11
<211> LENGTH: 23
<212> TYPE: DNA
<213> ORGANISM: Artificial Sequence
<220> FEATURE:

```
<223> OTHER INFORMATION: Synthetic sequence

<400> SEQUENCE: 11
gaatttcatc tgcatgtctt tgg                                              23

<210> SEQ ID NO 12
<211> LENGTH: 29
<212> TYPE: DNA
<213> ORGANISM: Artificial Sequence
<220> FEATURE:
<223> OTHER INFORMATION: Synthetic sequence

<400> SEQUENCE: 12
gatctatact acctcagtca aacagatgg                                        29

<210> SEQ ID NO 13
<211> LENGTH: 25
<212> TYPE: DNA
<213> ORGANISM: Artificial Sequence
<220> FEATURE:
<223> OTHER INFORMATION: Synthetic sequence

<400> SEQUENCE: 13
gaagccaaag atctgacaga gctgg                                            25

<210> SEQ ID NO 14
<211> LENGTH: 23
<212> TYPE: DNA
<213> ORGANISM: Artificial Sequence
<220> FEATURE:
<223> OTHER INFORMATION: Synthetic sequence

<400> SEQUENCE: 14
gcagatatgt tattctccgc tgg                                              23

<210> SEQ ID NO 15
<211> LENGTH: 90
<212> TYPE: DNA
<213> ORGANISM: Streptococcus pyogenes

<400> SEQUENCE: 15
atcttgttgg aaccattcaa aacagcatag caagttaaaa taaggctagt ccgttatcaa      60
cttgaaaaag tggcaccgag tcggtgcttt                                       90

<210> SEQ ID NO 16
<211> LENGTH: 264
<212> TYPE: DNA
<213> ORGANISM: Homo sapiens

<400> SEQUENCE: 16
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt     180
aaaatggact atcatatgct taccgtaact tgaaagtatt tcgatttctt ggctttatat     240
atcttgtgga aggacgaaa cacc                                             264

<210> SEQ ID NO 17
<211> LENGTH: 4116
<212> TYPE: DNA
<213> ORGANISM: Artificial Sequence
<220> FEATURE:
<223> OTHER INFORMATION: Synthetic sequence encoding Cas9 Protein
```

<400> SEQUENCE: 17

```
atggacaaga aatattcaat cggacttgac attggaacaa actctgtcgg ctgggccgtc    60
attactgatg agtacaaagt gccatccaag aagttcaaag tattgggcaa cacagatcgg   120
cacagtatca aaaaaaacct gatcggcgca ctgctgtttg actctggaga aaccgctgag   180
gctactagac ttaagcgcac tgcccggcgt aggtacacca ggagaaagaa tcgcatctgt   240
tatctgcagg agatctttag caacgaaatg gctaaggttg acgatagttt tttccaccgc   300
ctggaggaga gtttcctcgt agaggaggac aagaaacacg agcgtcaccc tattttcgga   360
aacatcgtgg atgaagtcgc ttaccacgag aagtatccta caatttatca cttgcgcaag   420
aaactcgtgg atagcacaga caaagctgac ctgcgcctta tctatctggc actggcacat   480
atgataaagt ttcgcgggca tttccttatt gagggagatt tgaatcccga taacagtgac   540
gtggataaac ttttcataca attggtccag acctataatc aactctttga agagaatcca   600
atcaacgcat ctggtgtgga cgctaaggcc attctcagtg cccggctgtc aaaatctagg   660
cgccttgaga atctgattgc acagctgccc ggggaaaaga gaacggctt gtttggaaat   720
ctgatcgctc tgtctctggg tctcacacct aatttcaagt caaatttcga cctggccgag   780
gatgcaaagc ttcagcttag caaagatacc tacgatgatg acctcgacaa tcttctcgcc   840
cagatcggcg accaatatgc tgacctgttc ctggccgcta agaatctgtc tgatgccatc   900
ctgctttctg atatcctgcg cgtcaatacc gaaataacca aggcaccact ttctgcttcc   960
atgattaaaa ggtacgacga gcatcaccaa gatctcactc tccttaaggc ccttgtgcgt  1020
cagcaactgc ccgaaaagta caagaaatc ttctttgacc agtctaagaa tgggtacgcc  1080
ggctacatcg atgaggcgc atcccaggaa gaattttata agttcattaa gcccatactg  1140
gaaaagatgg acggcactga ggaactgctt gtcaagctga acagagaaga tcttctgcgc  1200
aaacagcgta ccttcgataa tggttctatt ccacaccaaa ttcatctggg agagctccac  1260
gccattctcc ggagacaaga ggacttttat ccattcctga aggataatcg cgagaagatc  1320
gaaaagattc tcacatttcg gattccatac tacgttggcc cccttgcccg aggtaatagc  1380
cgttttgctt ggatgaccag gaagagtgag gaaaccatta cccttggaa ctttgaagaa  1440
gtggtagata agggagcctc cgcacaaagc tttattgagc gaatgactaa tttcgataag  1500
aatctgccaa acgaaaaagt cttgcctaaa cactccctgc tgtacgagta tttcacagtg  1560
tataacgagt tgacaaaagt caagtatgtt actgagggca tgcgaaaacc cgctttcctg  1620
tccggtgaac agaaaaaagc cattgtcgac ctgctctta aaactaaccg taaggtcacc  1680
gtcaaacaac ttaaggaaga ctattttaag aaaatcgagt gctttgactc cgttgagatt  1740
tccggagtag aagatcgatt caacgccagt ctgggtacat atcacgacct cctgaagata  1800
atcaaagaca aggattttct ggataatgag gagaatgagg acatactgga ggacattgtc  1860
ctgaccttga cctgttcga agaccggaa atgattgaag agaggctgaa acctacgcc  1920
cacctgttcg acgataaggt tatgaagcaa ctgaaacgta ggaggtacac tgggtggggc  1980
cgactttctc gtaagcttat taacggaatt agagataagc agtctggtaa gaccattctc  2040
gacttcctga aaagcgatgg ctttgctaac cgtaactta tgcagctgat tcacgacgat  2100
tctctgacat tcaaagaaga tatccagaaa gctcaagtct ctggtcaggg cgacagcctg  2160
cacgagcaca ttgcaaacct ggccggcagc ccagctatca agaagggaat acttcaaaca  2220
gtgaaggtgg tagacgagct ggtgaaggtc atgggtcgcc acaagccaga aaacatagta  2280
```

```
atcgagatgg cacgtgaaaa ccagacaacc cagaagggc agaagaattc tagagagcgg    2340
atgaaaagaa ttgaggaagg gatcaaggaa ctgggctctc agatcctcaa ggagcaccca    2400
gtagagaata cacagctcca aaatgaaaaa ctgtacttgt attacctgca aaacggcagg    2460
gacatgtacg tcgaccagga actggacatt aatcgcctga gtgattatga cgtcgaccat    2520
atcgtccctc agtccttcct gaaagatgat agcatcgaca caaagtcct cactcggtcc     2580 gacaaaaacc gtggcaagag cgacaatgtc ccttctgagg aagttgtgaa gaagatgaag    2640
aattattggc gtcagctcct gaatgcaaag ttgatcactc agaggaaatt cgacaatctc    2700
actaaggctg agcgaggagg gctgtccgag ctggacaaag ccggatttat caaacgtcaa    2760
ctcgttgaga ctcggcagat cactaagcac gtcgctcaaa tccttgattc agaatgaat     2820 accaagtacg atgaaaacga taagttgatc cgcgaggtga agtcattac actgaagtct     2880 aagctcgtgt ctgattttcg caaggacttc caattctata agtgaggga gatcaacaat     2940 tatcaccacg cccacgacgc ttatctcaat gctgtggtgg gcactgccct gatcaagaaa    3000
tatcccaaac tggagtcaga gtttgtgtat ggagattaca agtgtacga tgtgaggaag     3060 atgatcgcca agagcgagca ggagatcgga aaagcaacag ccaagtactt cttttacagc    3120
aatatcatga atttctttaa gaccgagatc accttggcca atggtgagat ccgaaaacgc    3180
cctctgatag agactaatgg cgaaactggt gagattgttt gggacaaggg aagagatttc    3240
gcaactgtga ggaaggtcct gtctatgccc caggtgaata tcgttaaaaa gaccgaggtg    3300
cagactggtg gcttcagtaa ggagtctatc ctgcctaagc gcaacagcga caaactgatt    3360
gcacgaaaga aggactggga ccccaagaaa tacgagggt cgacagccc taccgtggct     3420 tacagcgtgc ttgtggtcgc aaaggtggag aagggaaat ctaagaagct gaaaagtgtg     3480
aaagagctgc tgggcattac cattatgaa cggagttctt tcgagaagaa ccccatcgat     3540
tttctggaag ccaagggcta taggaagtt aaaaaggact tgattatcaa gctgcctaag     3600
tatagtttgt tcgaacttga aaacggtaga aaaaggatgc tcgcctccgc aggtgagctg    3660
cagaagggaa acgaattggc tctcccatcc aaatacgtga acttcttgta cctggccagc    3720
cattacgaaa aactcaaagg ctccccagag gacaacgaac agaagcagct gtttgtggaa    3780
caacataaac attacttgga cgaaataatc gagcagatca gcgagttttc caagagagtt    3840
atcctggccg atgcaaacct cgataaggtc ctttccgcct acaacaagca cagagacaaa    3900
ccaatccggg agcaggccga gaatattatc cacctgttca ccctgacaaa ccttggagca    3960
cctgctgcat tcaaatattt cgatactaca atcgatcgaa agcgctacac aagtaccaag    4020
gaggtgctgg acgccactct gatccatcag tccataactg gactgtatga aactcgtatc    4080
gatctgagcc agttgggggg agattctcgg gcagat                              4116
```

<210> SEQ ID NO 18
<211> LENGTH: 1372
<212> TYPE: PRT
<213> ORGANISM: Streptococcus pyogenes

<400> SEQUENCE: 18

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

```
Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
 65              70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
```

```
                465                 470                 475                 480
        Val Val Asp Lys Gly Ala Ser Ala Gln Ser Phe Ile Glu Arg Met Thr
                        485                 490                 495

Asn Phe Asp Lys Asn Leu Pro Asn Glu Lys Val Leu Pro Lys His Ser
                        500                 505                 510

Leu Leu Tyr Glu Tyr Phe Thr Val Tyr Asn Glu Leu Thr Lys Val Lys
                        515                 520                 525

Tyr Val Thr Glu Gly Met Arg Lys Pro Ala Phe Leu Ser Gly Glu Gln
                        530                 535                 540

Lys Lys Ala Ile Val Asp Leu Leu Phe Lys Thr Asn Arg Lys Val Thr
        545                 550                 555                 560

Val Lys Gln Leu Lys Glu Asp Tyr Phe Lys Lys Ile Glu Cys Phe Asp
                        565                 570                 575

Ser Val Glu Ile Ser Gly Val Glu Asp Arg Phe Asn Ala Ser Leu Gly
                        580                 585                 590

Thr Tyr His Asp Leu Leu Lys Ile Ile Lys Asp Lys Asp Phe Leu Asp
                        595                 600                 605

Asn Glu Glu Asn Glu Asp Ile Leu Glu Asp Ile Val Leu Thr Leu Thr
                        610                 615                 620

Leu Phe Glu Asp Arg Glu Met Ile Glu Glu Arg Leu Lys Thr Tyr Ala
        625                 630                 635                 640

His Leu Phe Asp Asp Lys Val Met Lys Gln Leu Lys Arg Arg Arg Tyr
                        645                 650                 655

Thr Gly Trp Gly Arg Leu Ser Arg Lys Leu Ile Asn Gly Ile Arg Asp
                        660                 665                 670

Lys Gln Ser Gly Lys Thr Ile Leu Asp Phe Leu Lys Ser Asp Gly Phe
                        675                 680                 685

Ala Asn Arg Asn Phe Met Gln Leu Ile His Asp Asp Ser Leu Thr Phe
                        690                 695                 700

Lys Glu Asp Ile Gln Lys Ala Gln Val Ser Gly Gln Gly Asp Ser Leu
        705                 710                 715                 720

His Glu His Ile Ala Asn Leu Ala Gly Ser Pro Ala Ile Lys Lys Gly
                        725                 730                 735

Ile Leu Gln Thr Val Lys Val Val Asp Glu Leu Val Lys Val Met Gly
                        740                 745                 750

Arg His Lys Pro Glu Asn Ile Val Ile Glu Met Ala Arg Glu Asn Gln
                        755                 760                 765

Thr Thr Gln Lys Gly Gln Lys Asn Ser Arg Glu Arg Met Lys Arg Ile
                        770                 775                 780

Glu Glu Gly Ile Lys Glu Leu Gly Ser Gln Ile Leu Lys Glu His Pro
        785                 790                 795                 800

Val Glu Asn Thr Gln Leu Gln Asn Glu Lys Leu Tyr Leu Tyr Tyr Leu
                        805                 810                 815

Gln Asn Gly Arg Asp Met Tyr Val Asp Gln Glu Leu Asp Ile Asn Arg
                        820                 825                 830

Leu Ser Asp Tyr Asp Val Asp His Ile Val Pro Gln Ser Phe Leu Lys
                        835                 840                 845

Asp Asp Ser Ile Asp Asn Lys Val Leu Thr Arg Ser Asp Lys Asn Arg
                        850                 855                 860

Gly Lys Ser Asp Asn Val Pro Ser Glu Glu Val Val Lys Lys Met Lys
        865                 870                 875                 880

Asn Tyr Trp Arg Gln Leu Leu Asn Ala Lys Leu Ile Thr Gln Arg Lys
                        885                 890                 895
```

-continued

```
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
```

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Arg Ala Asp
    1370

<210> SEQ ID NO 19
<211> LENGTH: 21
<212> TYPE: DNA
<213> ORGANISM: Simian virus 40

<400> SEQUENCE: 19
cccaagaaga agaggaaggt g                                         21

<210> SEQ ID NO 20
<211> LENGTH: 7
<212> TYPE: PRT
<213> ORGANISM: Simian virus 40

<400> SEQUENCE: 20

Pro Lys Lys Lys Arg Lys Val
1               5

<210> SEQ ID NO 21
<211> LENGTH: 36
<212> TYPE: DNA
<213> ORGANISM: Streptococcus pyogenes

<400> SEQUENCE: 21
gttttagagc tatgctgttt tgaatggtcc caaaac                         36

<210> SEQ ID NO 22
<211> LENGTH: 451
<212> TYPE: PRT
<213> ORGANISM: Artificial Sequence
<220> FEATURE:
<223> OTHER INFORMATION: Rituximab heavy chain amino acid sequence

<400> SEQUENCE: 22

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 23
<211> LENGTH: 2051
<212> TYPE: DNA
<213> ORGANISM: Artificial Sequence
<220> FEATURE:
<223> OTHER INFORMATION: Rituximab heavy chain nucleic acid sequence

<400> SEQUENCE: 23
atgtatctgg gattgaattg cgtcattatc gtgtttctgc tcaagggtgt gcaaagtcag    60

| | |
|---|---|
| gtccagctgc agcagccagg cgcagagctg gttaagccag gagcctcagt gaaaatgagc | 120 |
| tgcaaagcct ctggctacac ctttaccagc tataacatgc attgggtgaa acagacaccc | 180 |
| ggcagagggc tggaatggat cggagccata taccccggga acggggacac ctcctataac | 240 |
| cagaagttca agggaaaggc cacactcact gctgacaagt ccagtagcac cgcttacatg | 300 |
| caactttcaa gcttgacatc agaggattct gcagtttact actgtgcccg gtctacttac | 360 |
| tatggcggcg attggtattt caatgtatgg ggtgctggca acagtcac tgtgagcgca | 420 |
| gctagcacca agggcccatc ggtcttcccc ctggcaccct cctccaagag cacctctggg | 480 |
| ggcacagcgg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagaa agttggtgag | 720 |
| aggccagcac agggagggag ggtgtctgct ggaagccagg ctcagcgctc ctgcctggac | 780 |
| gcatcccggc tatgcagccc cagtccaggg cagcaaggca ggccccgtct gcctcttcac | 840 |
| ccggaggcct ctgcccgccc cactcatgct cagggagagg tcttctggc tttttcccca | 900 |
| ggctctgggc aggcacaggc taggtgcccc taacccaggc cctgcacaca aggggcagg | 960 |
| tgctgggctc agacctgcca agagccatat ccgggaggac cctgcccctg acctaagccc | 1020 |
| accccaaagg ccaaactctc cactccctca gctcggacac tttctctcct cccagattcc | 1080 |
| agtaactccc aatcttctct ctgcagagcc caaatcttgt gacaaaactc acacatgccc | 1140 |
| accgtgccca ggtaagccag cccaggcctc gccctccagc tcaaggcggg acaggtgccc | 1200 |
| tagagtagcc tgcatccagg acaggcccc agccgggtgc tgacacgtcc acctccatct | 1260 |
| cttcctcagc acctgaactc ctggggggac cgtcagtctt cctcttcccc ccaaaaccca | 1320 |
| aggacaccct catgatctcc cggacccctg aggtcacatg cgtggtggtg gacgtgagcc | 1380 |
| acgaagaccc tgaggtcaag ttcaactggt acgtggacgg cgtggaggtg cataatgcca | 1440 |
| agacaaagcc gcgggaggag cagtacaaca gcacgtaccg tgtggtcagc gtcctcaccg | 1500 |
| tcctgcacca ggactggctg aatggcaagg agtacaagtg caaggtctcc aacaaagccc | 1560 |
| tcccagcccc catcgagaaa accatctcca agccaaagg tgggaccgt ggggtgcgag | 1620 |
| ggccacatgg acagaggccg gctcggcccc ataacttcgt atagcataca ttatacgaag | 1680 |
| ttatacctc tgccctgaga gtgaccgctg taccaacctc tgtccctaca gggcagcccc | 1740 |
| gagaaccaca ggtgtacacc ctgcccccat cccgggatga gctgaccaag aaccaggtca | 1800 |
| gcctgacctg cctggtcaaa ggcttctatc ccagcgacat cgccgtggag tgggagagca | 1860 |
| atgggcagcc ggagaacaac tacaagacca cgcctcccgt gctggactcc gacggctcct | 1920 |
| tcttcctcta cagcaagctc accgtggaca agagcaggtg gcagcagggg aacgtcttct | 1980 |
| catgctccgt gatgcatgag gctctgcaca accactacac gcagaagagc ctctccctgt | 2040 |
| ctccgggtaa a | 2051 |

<210> SEQ ID NO 24
<211> LENGTH: 213
<212> TYPE: PRT
<213> ORGANISM: Artificial Sequence
<220> FEATURE:
<223> OTHER INFORMATION: Rituximab light chain amino acid sequence

<400> SEQUENCE: 24

Gln Ile Val Leu Ser Gln Ser Pro Ala Ile Leu Ser Ala Ser Pro Gly

```
              1               5                  10                 15
           Glu Lys Val Thr Met Thr Cys Arg Ala Ser Ser Val Ser Tyr Ile
                           20                 25                 30
           His Trp Phe Gln Gln Lys Pro Gly Ser Ser Pro Lys Pro Trp Ile Tyr
                           35                 40                 45
           Ala Thr Ser Asn Leu Ala Ser Gly Val Pro Val Arg Phe Ser Gly Ser
           50                              55                 60
           Gly Ser Gly Thr Ser Tyr Ser Leu Thr Ile Ser Arg Val Glu Ala Glu
           65                 70                 75                 80
           Asp Ala Ala Thr Tyr Tyr Cys Gln Gln Trp Thr Ser Asn Pro Pro Thr
                              85                 90                 95
           Phe Gly Gly Gly Thr Lys Leu Glu Ile Lys Arg Thr Val Ala Ala Pro
                           100                105                110
           Ser Val Phe Ile Phe Pro Pro Ser Asp Glu Gln Leu Lys Ser Gly Thr
                           115                120                125
           Ala Ser Val Val Cys Leu Leu Asn Asn Phe Tyr Pro Arg Glu Ala Lys
                           130                135                140
           Val Gln Trp Lys Val Asp Asn Ala Leu Gln Ser Gly Asn Ser Gln Glu
           145                150                155                160
           Ser Val Thr Glu Gln Asp Ser Lys Asp Ser Thr Tyr Ser Leu Ser Ser
                              165                170                175
           Thr Leu Thr Leu Ser Lys Ala Asp Tyr Glu Lys His Lys Val Tyr Ala
                           180                185                190
           Cys Glu Val Thr His Gln Gly Leu Ser Ser Pro Val Thr Lys Ser Phe
                           195                200                205
           Asn Arg Gly Glu Cys
                 210
```

<210> SEQ ID NO 25
<211> LENGTH: 705
<212> TYPE: DNA
<213> ORGANISM: Artificial Sequence
<220> FEATURE:
<223> OTHER INFORMATION: Rituximab light chain nucleic acid sequence

<400> SEQUENCE: 25

| | | | | | | |
|---|---|---|---|---|---|---|
| atggatatga | gggtaccagc | acaacttctc | ggattactat | tgttatggct | gcgaggtgcg | 60 |
| cgctgtcaga | ttgtcttgag | ccagtctccc | gccattttgt | ctgcctcccc | tggggagaaa | 120 |
| gtaaccatga | cttgtcgcgc | atcctcaagc | gtgagttaca | tccactggtt | tcagcagaag | 180 |
| cctggcagct | cacccaagcc | ctggatctat | gctacctcca | acctcgcttc | cggagtgcct | 240 |
| gtgcggtttt | ctgggtccgg | tagtggtacc | agctactcac | tgactatttc | aagagttgag | 300 |
| gctgaagatg | ccgcaaccta | ttactgccaa | cagtggacaa | gtaatccacc | aacattcggt | 360 |
| ggcggcacta | aactggagat | caagcgtacg | gtggctgcac | catctgtctt | catcttcccg | 420 |
| ccatctgatg | agcagttgaa | atctggaact | gcctctgttg | tgtgcctgct | gaataacttc | 480 |
| tatcccagag | aggccaaagt | acagtggaag | gtggataacg | ccctccaatc | gggtaactcc | 540 |
| caggagagtg | tcacagagca | ggacagcaag | gacagcacct | acagcctcag | cagcaccctg | 600 |
| acgctgagca | agcagactac | gagaaacac | aaagtctacg | cctgcgaagt | cacccatcag | 660 |
| ggcctgagtt | caccggtgac | aaagagcttc | aacaggggag | agtgt | | 705 |

<210> SEQ ID NO 26
<211> LENGTH: 469
<212> TYPE: PRT

<213> ORGANISM: Artificial Sequence
<220> FEATURE:
<223> OTHER INFORMATION: Trastuzumab heavy chain amino acid sequence

<400> SEQUENCE: 26

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
```

```
                385                 390                 395                 400
Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 27
<211> LENGTH: 2008
<212> TYPE: DNA
<213> ORGANISM: Artificial Sequence
<220> FEATURE:
<223> OTHER INFORMATION: Trastuzumab heavy chain nucleic acid sequence

<400> SEQUENCE: 27
atggagctgt atcatcctct tcttggtagc aacagctaca ggtgtccact ccgaggttca      60
gctggtggag tctggcggtg gcctggtgca gccagggggc tcactccgtt tgtcctgtgc     120
agcttctggc ttcaacatta agacaccta tatacactgg gtgcgtcagg ccccgggtaa     180
gggcctggaa tggttgcaa ggatttatcc tacgaatggt tatactagat atgccgatag     240
cgtcaagggc cgtttcacta taagcgcaga cacatccaaa aacacagcct acctgcagat     300
gaacagcctg cgtgctgagg acactgccgt ctattattgt tccagatggg aggggacgg     360 cttctatgct atggactact ggggtcaagg aaccctggtc accgtctcct cggctagcac     420
caagggccca tcggtcttcc ccctggcacc ctcctccaag agcacctctg ggggcacagc     480
ggccctgggc tgcctggtca aggactactt ccccgaaccg gtgacggtgt cgtggaactc     540
aggcgccctg accagcggcg tgcacacctt cccggctgtc ctacagtcct caggactcta     600
ctccctcagc agcgtggtga ccgtgccctc cagcagcttg ggcacccaga cctacatctg     660
caacgtgaat cacaagccca gcaacaccaa ggtggacaag aaagttggtg agaggccagc     720
acagggaggg agggtgtctg ctggaagcca ggctcagcgc tcctgcctgg acgcatcccg     780
gctatgcagc cccagtccag ggcagcaagg caggccccgt ctgcctcttc acccggaggc     840
ctctgcccgc ccactcatg ctcagggaga gggtcttctg gctttttccc caggctctgg     900
gcaggcacag gctaggtgcc cctaacccag gccctgcaca aaggggca ggtgctgggc     960 tcagacctgc caagagccat atccgggagg accctgcccc tgacctaagc ccaccccaaa    1020
ggccaaactc tccactccct cagctcggac accttctctc ctcccagatt ccagtaactc    1080
ccaatcttct ctctgcagag cccaaatctt gtgacaaaac tcacacatgc ccaccgtgcc    1140
caggtaagcc agcccaggcc tcgccctcca gctcaaggcg ggacaggtgc cctagagtag    1200
cctgcatcca gggacaggcc ccagccgggt gctgacacgt ccacctccat ctcttcctca    1260
gcacctgaac tcctggggg accgtcagtc ttcctcttcc cccaaaaacc caaggacacc    1320
ctcatgatct cccggacccc tgaggtcaca tgcgtggtgg tggacgtgag ccacgaagac    1380
cctgaggtca agttcaactg gtacgtggac ggcgtggagg tgcataatgc caagacaaag    1440
ccgcgggagg agcagtacaa cagcacgtac cgtgtggtca gcgtcctcac cgtcctgcac    1500
caggactggc tgaatggcaa ggagtacaag tgcaaggtct ccaacaaagc cctcccagcc    1560
```

| | |
|---|---|
| cccatcgaga aaaccatctc caaagccaaa ggtgggaccc gtggggtgcg agggccacat | 1620 |
| ggacagaggc cggctcggcc caccctctgc cctgagagtg accgctgtac caacctctgt | 1680 |
| ccctacaggg cagccccgag aaccacaggt gtacaccctg cccccatccc gggaggagat | 1740 |
| gaccaagaac caggtcagcc tgacctgcct ggtcaaaggc ttctatccca gcgacatcgc | 1800 |
| cgtggagtgg gagagcaatg ggcagccgga gaacaactac aagaccacgc ctcccgtgct | 1860 |
| ggactccgac ggctccttct tcctctacag caagctcacc gtggacaaga gcaggtggca | 1920 |
| gcaggggaac gtcttctcat gctccgtgat gcatgaggct ctgcacaacc actacacgca | 1980 |
| gaagagcctc tccctgtctc cgggtaaa | 2008 |

```
<210> SEQ ID NO 28
<211> LENGTH: 233
<212> TYPE: PRT
<213> ORGANISM: Artificial Sequence
<220> FEATURE:
<223> OTHER INFORMATION: Trastuzumab light chain amino acid sequence

<400> SEQUENCE: 28
```

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Asp Val
            35                  40                  45

Asn Thr Ala Val Ala Trp Tyr Gln Gln Lys Pro Gly Lys Ala Pro Lys
        50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

```
<210> SEQ ID NO 29
<211> LENGTH: 699
<212> TYPE: DNA
<213> ORGANISM: Artificial Sequence
<220> FEATURE:
<223> OTHER INFORMATION: Trastuzumab light chain nucleic acid sequence
```

```
<400> SEQUENCE: 29
atgggatgga gctgtatcat cctcttcttg gtagcaacag ctacaggtgt ccactccgat      60
attcagatga cccagtcccc gagctccctg tccgcctctg tgggcgatag ggtcaccatc     120
acctgccgtg ccagtcagga tgtgaatact gctgtagcct ggtatcaaca gaaaccagga     180
aaagctccga aactactgat ttactcggca tccttcctct actctggagt cccttctcgc     240
ttctctggtt ccagatctgg gacggatttc actctgacca tcagcagtct gcagccggaa     300
gacttcgcaa cttattactg tcagcaacat tatactactc ctcccacgtt cggacagggt     360
accaaggtgg agatcaaacg tacggtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgt                           699
```

METHODS AND COMPOSITIONS FOR PRODUCING DOUBLE ALLELE KNOCK OUTS

CROSS REFERENCE TO RELATED APPLICATIONS

This application is a continuation of application Ser. No. 14/335,903 filed Jul. 19, 2014, which claims benefit of U.S. Provisional application Ser. No. 61/856,579, filed Jul. 19, 2013, the contents of which are incorporated herein by reference in its entirety.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "LRX.0003_ST25.txt", a creation date of Jul. 19, 2014, and a size of 42 kilobytes. The Sequence Listing filed via EFS-Web is part of the specification and is hereby incorporated in its entirety by reference herein

BACKGROUND OF THE INVENTION

Gene knock out technology has been shown to be enormously valuable in biological research. Conventional gene disruption technology by homologous recombination is a laborious and unpredictable process. The targeted genome editing developed in recent years is much more effective and may be achieved by targeted double strand breakage (DSB) in chromosomes. Examples of this technique utilize Clustered Regularly Interspaced Short Palindromic Repeat (CRISPR), zinc-finger nucleases (ZFN) or transcription activator-like effector nucleases (TALEN) (Esvelt and Wang, *Mol. Syst. Biol.*, 2013, 9:641). Among these, CRISPR is the most versatile genome editing tool because of its targeting mechanism by specific RNA sequence complementary to the genome modification site. CRISPR permits genome editing in multiple sites by using a cluster of targeting RNA sequences. DSB in cells is repaired by non-homologous end joining (NHEJ), which in low frequency, results in small insertion or deletion (indel) that may create a frameshift and inactivate the gene of interest.

Using most methods, the rate of genome editing is relatively low, typically less than 5%. The most common methods of assessing genome editing, detecting duplex DNA mismatch utilizing the Surveyor® nuclease assay (Transgenomic, Inc., Omaha, Nebr.) or deep sequencing, do not differentiate single allele or double allele mutations. Since the possibility of producing a double allele mutation in a single step is negligible, 2-step sequential genome editing is usually required.

Therapeutic antibodies are a successful new class of drugs developed in the past two decades. Over thirty recombinant therapeutic antibodies have been approved by the FDA for the treatment of various diseases including cancer, viral infection, organ graft rejection, rheumatoid arthritis and other autoimmune conditions. Many more therapeutic antibodies are in clinical trials for an ever-widening variety of diseases. With the advent of molecular biology, it has become possible to produce recombinant antibodies in mammalian cells (N. Yamane-Ohnuki and M. Satoh, *mAbs*, 2009, 1(3):230-236).

Antibody therapy directed against soluble factors, such as vascular endothelial growth factor or tumor necrosis factor, aims simply to reduce the free ligand concentration by immunocomplex formation. In contrast, when antibody therapy is directed at cell surface antigens, as is usually the case in antineoplastic immunotherapy, the goal is typically the removal of the disease-causing cell itself. Antibody-dependent cellular cytotoxicity (ADCC), a lytic attack on antibody-targeted cells, is triggered upon binding of lymphocyte receptors (e.g., FcγRs) by the constant region (Fc) of the antibodies, in most cases, immunoglobulin subclass 1 (IgG1). ADCC is considered to be a major function of some of the therapeutic antibodies, although antibodies have multiple therapeutic functions (e.g., antigen binding, induction of apoptosis, and complement-dependent cellular cytotoxicity) (T. Shinkawa, et al., *J. Bio. Chem.*, 2003, 278(5):3466-3473). In ADCC, natural killer (NK) cells recognize the constant (Fc) region of antibodies primarily via interaction with the NK cell's FcγRIII receptor, which then activates cell lysis and apoptosis.

The Fc-FcγRIII interaction is extremely sensitive to Fc glycosylation. Aglycosylated antibodies, e.g., those produced by non-mammalian cell lines, fail to bind Fc receptors (Leatherbarrow et al., *Mol. Immun.*, 1985, 22:407-15; Walker et al., *Biochem. J.*, 1989, 259:347-53; Leader et al., *Immunology*, 1991, 72:481-5). On the other hand, fucosylation of the carbohydrate chain attached to Asn297 of the Fc region reduces binding to FcγRIII and reduces in vitro ADCC activity (Shields et al., *J. Biol. Chem.*, 2002, 277: 26733-40; Shinkawa et al., *J. Biol. Chem.*, 2003, 278:3466-73; Niwa et al., *Cancer Res.*, 2004, 64:2127-33).

The majority of mammalian immunoglobulins are fucosylated, including those produced by Chinese hamster ovary cells (CHO cells) (Jefferis et al., *Biochem J.*, 1990, 268:529-37; Raju et al., *Glycobiology*, 2000, 10:477-86). Fucose is attached to the Fc core region via an α-1,6 linkage generated by the α-1,6 fucosyltransferase (FUT8) protein (Oriol et al., *Glycobiology*, 1999, 9:323-34; Costache et al., *J. Biol. Chem.*, 1997, 272:29721-8). Disruption of the Fut8 gene in CHO cells can eliminate core fucosylation of antibodies and can increase ADCC ~100 folds (Yamane-Ohnuki et al., *Biotech. Bioengin.*, 2004, 87(5):614-622).

Genome editing has been used to reduce or eliminate FUT8 activity by knocking down or knocking out both Fut8 alleles. Imai-Nishiya et al. have disclosed the double knock-down of Fut8 and GMD, using a siRNA tandem expression vector for targeting these genes and introducing it into IgG1 antibody-producing CHO/DG44 32-05-12 cells (*BMC Biotechnology*, 2007, 7:84; doi:10.1186/1472-6750-7-84). To create double allele Fut8 knock-out CHO cells, Yamane-Ohnuki et al. disclosed a two-step sequential homologous recombination process (*Biotech. Bioengin.*, 2004, 87(5): 614-622) to overcome the low frequency of homologous recombination. Similarly, Collingwood disclosed a targeted ZFN method to knock out both Fut8 alleles in CHOK cells by continuous culturing in the presence of a lethal dosage of *Lens culinaris* Agglutinin (LCA) to enrich Fut8 null cells, taking advantage of cell toxicity induced by specific binding of LCA to fucose (WO 2009/009086; L. Malphettes et al., *Biotech. Bioengin.*, 2010, 106(5):774-783).

Further, it may be desirable to produce cells lines in which other genes in addition to the Fut8 gene are partially or fully suppressed. Because the rate of genomic editing is low, typically less than 5%, it is reasonable to assume that the possibility of producing a double allele mutation by a single crRNA site is negligible. One may have to perform sequential genome editing in order to obtain double allele knock-outs. For example, Cong, et al. disclosed successful genome editing in two endogenous genes (EMX1 and PVALB) and two targeting sites in the same EMX1 gene (*Science*, 2013, 339:819-823). However, the efficiency of deletion was only 1.6% when 2 protospacers in the EMX1 gene were targeted, and no double allele knock-outs were reported.

SUMMARY OF THE INVENTION

In one aspect, the present invention provides a method of producing a double allele knock-out in a eukaryotic cell by providing said cells with a CRISPR system comprising a nuclease and at least two targeting RNAs that are complementary to the DNA spacer sequences in the target gene. In an embodiment, the same tracrRNA may be used with multiple, different crRNAs, and the many crRNAs can be organized with a single tracrRNA. In an embodiment, the CRISPR system comprises at least three or four targeting RNAs. In an embodiment, the multiple CRISPR targets (crRNA targets) are in the same gene. In an embodiment, the multiple CRISPR targets are in the same exon of the gene. In an embodiment, the multiple CRISPR targets are within 500 bp, 450 bp, 400 bp, 375 bp, 350, bp, 300 bp, 250 bp, 200 bp, 150 bp, 100 bp, or 50 bp of the gene. In one embodiment, the eukaryotic cells are mammalian. In another embodiment, the mammalian cells are CHO cells, CHOS cells, 293 cells, NS0 cells, embryonic stem cells, or derivatives thereof, or antibody-producing cells or derivatives thereof. In a further embodiment, the nuclease is a Cas variant. In another embodiment, the Cas variant nuclease is Cas9. In one embodiment, the targeting RNA is comprised of tracrRNA and crRNA. In another embodiment, the tracrRNA and the crRNA may be connected by a hairpin RNA linkage. In a further embodiment, the targeted gene is a fucosyltransferase. In another embodiment, the targeted fucosyltransferase gene is Fut8, alpha-(1-6)-fucosyltransferase. In a further embodiment, the targeted gene is glutamine synthetase. In another embodiment, the targeted gene is dihydrofolate reductase (DHFR). In another embodiment, the targeted gene is a sialidase.

In another aspect, the present invention comprises mammalian cells having Fut8 knocked out using the methods of the invention. In one embodiment, the mammalian cells comprise Fut8 knock-out cells that are isolated by FACS for negative fluorescence signal after fluorescence labeling of cell surface fucose. In one embodiment, the fluorescence labeling comprises binding with fluorescein-labeled *L. culinaris* agglutinin (LCA-FITC).

In a further aspect, the present invention comprises mammalian cells having glutamine synthetase knocked out using the methods of the invention.

In another aspect, the present invention comprises mammalian cells having DHFR knocked out using methods of the invention.

In another aspect, the present invention comprises mammalian cells having a sialidase knocked out using the methods of the invention.

In another aspect, the present invention comprises mammalian cells having other target genes knocked out using the methods of the invention.

In a further aspect, the present invention comprises afucosylated proteins produced by eukaryotic cells having Fut8 knocked out using methods of the present invention. In one embodiment, the afucosylated proteins are antibodies. In a further embodiment, the antibody is rituximab.

In another aspect, the present invention comprises a plasmid comprising nucleotides encoding a Cas9 protein, and either one or both of crRNA and tracrRNA, wherein the plasmid is a mammalian cell expression vector, and wherein when both crRNA and tracrRNA are present, they are optionally connected by a hairpin RNA linkage. In one embodiment, the plasmid comprises one or both crRNA and tracrRNA, wherein partial sequences of either crRNA or tracrRNA capable of targeting a Cas9 chromosomal site are utilized. In a further embodiment, the crRNA is comprised of at least two protospacer sequences of a targeted gene. In another embodiment, the Cas9 protein expression is expressed by a promoter. In a further embodiment, the promoter is a CMV promoter. In another embodiment, the tracrRNA is expressed by a promoter. In a further embodiment, the crRNA is expressed by a promoter. In another embodiment, the crRNA connected with tracrRNA by a hairpin RNA linkage is expressed by a promoter. In further embodiments, the tracrRNA promoter and the crRNA promoter is a human U6 promoter. In another embodiment, the plasmid further comprises an antibiotic resistant gene. In a further embodiment, the antibiotic is ampicillin.

In a further aspect, the present invention provides a method wherein the cells of the invention are transfected with at least one plasmid containing Cas9.

In another aspect, the present invention provides a method wherein the cells of the invention are transfected with at least one plasmid containing crRNA.

In a further aspect, the present invention provides a method wherein the cells of the invention are transfected with at least one plasmid containing crRNA connected with tracrRNA by a hairpin RNA linkage.

BRIEF DESCRIPTION OF THE DRAWINGS

FIG. 1A shows a typical CRISPR system has three components: the Cas9 protein and two small RNAs, crRNA and tracrRNA; crRNA contains a sequence complementary to the targeted DNA (spacer sequence plus NGG); tracrRNA contains a sequence complementary to the crRNA; wild-type Cas9 leads to double strand DNA break whereas Cas9-D10A leads to single strand DNA break. FIG. 1B shows the modified CRISPR system of the present invention has two components: the Cas9 protein and a single gRNA which combines sequences of crRNA and tracrRNA, where the gRNA contains a sequence complementary to the targeted DNA and a hairpin structure. FIG. 1C shows a schematic drawing of crRNA containing 3 different targeting spacers; DR refers to the direct repeat while T1, T2, and T3 are the targeting sequences.

FIG. 2A shows the vector LB200. FIG. 2B shows the vector LB221 in which a IRES-GFP cassette was inserted after Cas9.

FIG. 4A shows the negative control CHOS cells without LCA-FITC staining and the positive control fucose staining with LCA-FITC in wild type CHOS cells. FIG. 4B shows LCA-FITC staining of fucose on CHOS cells after introduction of CRISPR systems with a single targeting RNA or crRNA.

FIG. 5A shows the negative control CHOS cells without LCA-FITC staining and the positive control fucose staining with LCA-FITC in wild type CHOS cells. FIG. 5B shows LCA-FITC staining of fucose on CHOS cells after introduction of CRISPR systems with one (1) to ten (10) targeting RNAs or crRNAs. FIG. 5C shows CHOS cells before and after LCA-FITC staining, and LAC-FITC staining of cells cloned from the M2 pool of transfection #5 (three target RNAs), labeled 2.123.3P and transfection #6 (four target RNAs) labeled 2.123.4P.

FIG. 7 shows a glycan analysis of rituximab (Rituxan) and trastuzumab (Herceptin) made in wild-type CHOS cells, and CHOS cells with double allele knock-outs of Fut8.

FIG. 8A shows the ADCC activity of rituximab (Rituxan) made in wild-type CHOS cells, and CHOS cells with double allele knock-outs of Fut8. FIG. 8B shows ADCC activity of trastuzumab (Herceptin) made in wild-type CHOS cells, and CHOS cells with double allele knock-outs of Fut8.

DETAILED DESCRIPTION OF THE INVENTION

Figure 1A:
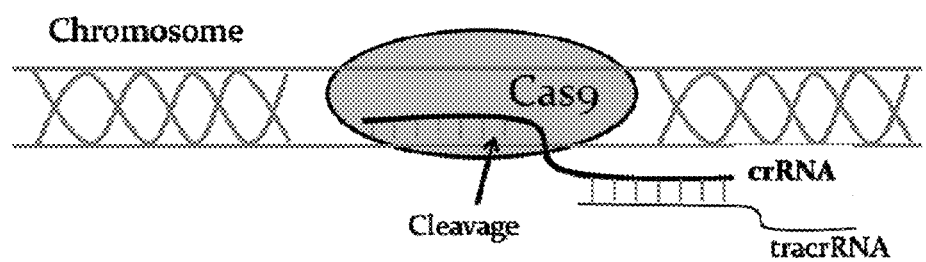
FIG. 1A-C schematically depicts Cas9 mediated sequence specific DNA cleavage.
Figure 1B:
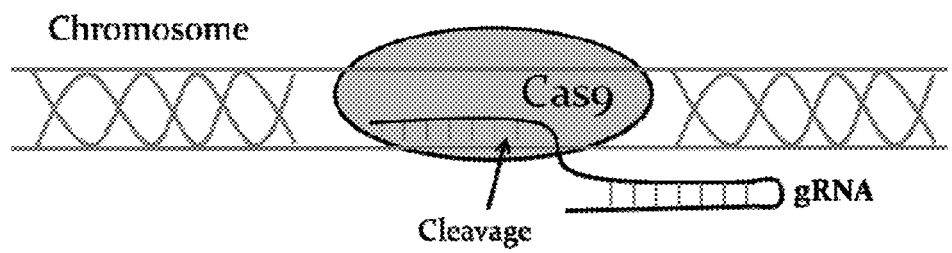

The invention is illustrated by way of example and not by way of limitation. It should be noted that references to "an" or "one" or "some" embodiment(s) in this disclosure are not necessarily to the same embodiment, and all such references mean at least one. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

Generally, nomenclatures used in connection with, and techniques of, cell and tissue culture, molecular biology, immunology, microbiology, genetics and protein and nucleic acid chemistry and hybridization described herein are well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art, or as described herein. So that the present invention may be more readily understood, selected terms are defined below.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule, including for example, one or more polypeptides substantially encoded by immunoglobulin genes, fragments of immunoglobulin genes, hybrid immunoglobulin genes (made by combining the genetic information from different animals), or synthetic immunoglobulin genes, or a single-chain antibody, a Fab, a F(ab)$_2$, a scFv, a dAB, a VHH, a camelid antibody, or a nanobody. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG 4, IgA1 and IgA2) or subclass.

An "isolated antibody", as used herein, is intended to refer to an antibody that is substantially free of other antibodies having different antigenic specificities (e.g., an isolated antibody that specifically binds the CD20 antigen found on the surface of normal and malignant B lymphocytes). An isolated antibody that specifically binds the CD20 antigen may, however, have cross-reactivity to other antigens, such as the CD20 molecules from other species. Moreover, an isolated antibody may be substantially free of other cellular material and/or chemicals.

The term "polynucleotide" as referred to herein means a polymeric form of two or more nucleotides, either ribonucleotides or deoxyribonucleotides or a modified form of either type of nucleotide. The term includes single and double stranded forms of DNA, but particularly is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, which serve equivalent functions. Inside cells, vectors and/or plasmids may exist extra-chromosomally or integrated into host cell DNA.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences, which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

The terms "introducing a purified DNA into a eukaryotic host cell" or "transfection" denote any process wherein an extracellular DNA, with or without accompanying material, enters a host cell. The term "cell transfected" or "transfected cell" means the cell into which the extracellular DNA has been introduced and thus harbors the extracellular DNA. The DNA might be introduced into the cell so that the nucleic acid is replicable either as a chromosomal integrant or as an extra chromosomal element. "Promoter" as used herein refers to a nucleic acid sequence that regulates expression of a gene.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Particularly host cells include eukaryotic cells.

"Eukaryotic cell" refers to any mammalian or non-mammalian cell from a eukaryotic organism. By way of non-limiting example, any eukaryotic cell that is capable of being maintained under cell culture conditions and subsequently transfected would be included in this invention. Especially preferable cell types include, e.g., stem cells, embryonic stem cells, Chinese hamster ovary cells (CHO), 293 cells, NS0 cells, COS, BHK21, NIH3T3, HeLa, C2Cl2, cancer cells, plant cells, fungal cells, and primary differentiated or undifferentiated cells. Other suitable host cells are known to persons of ordinary skill in the art.

The "gene of interest" or "transgene" preferably encodes a protein (structural or regulatory protein). As used herein "protein" refers generally to peptides and polypeptides having more than about ten amino acids. The proteins may be "homologous" to the host (i.e., endogenous to the host cell being utilized), or "heterologous," (i.e., foreign to the host cell being utilized), such as a human protein produced by yeast. The protein may be produced as an insoluble aggregate or as a soluble protein in the periplasmic space or cytoplasm of the cell, or in the extracellular medium.

Standard techniques may be used for recombinant DNA, oligonucleotide synthesis, tissue culture and transformation (e.g., electroporation, lipofection). Enzymatic reactions and purification techniques may be performed according to manufacturer's specifications or as commonly accomplished in the art, or as described herein. The foregoing techniques and procedures may be generally performed according to conventional methods well known in the art and as described in various general and more specific references that are cited and discussed throughout the present specification. Illustrative methods are described in *Current Protocols in Immunology* (Edited by: Coligan, J. E., et al., John Wiley & Sons, NY, N.Y., 2001), Ausubel et al., *Current Protocols in Molecular Biology*, Greene Publ. Assoc. Inc. & John Wiley & Sons, Inc., NY, N.Y., 2001), Sambrook et al. (*Molecular Cloning*, 3rd Ed., Cold Spring Harbor Laboratory, Plainview, N.Y., 2001) and elsewhere.

Overview of the Invention

The present invention utilizes the CRISPR system to disrupt a target gene in eukaryotic cells. More specifically, the system transiently expresses Cas9, tracrRNA (single or multiple), and multiple crRNAs targeting multiple exon sites of a gene of interest in a eukaryotic cell such as CHO cells, 293 cells, NS0 cells, or any antibody producing cells. The main advantage of the system of the present invention compared to published CRISPR methods is that it specifically knocks out two targeted alleles in one step by using multiple crRNA sequences in the same system. Most of the publications related to CRISPR utilize the Surveyor® nuclease assay (Transgenomic, Inc., Omaha, Nebr.) or deep sequencing to assess genome editing rates and do not differentiate single allele or double allele mutations. The present approach to efficient double allele genome editing targets the same gene/exon with multiple crRNA targets. Without wishing to be bound by any particular theory, we hypothesized that targeting multiple crRNA sites would significantly enhance the possibility of producing double allele knock-outs. Indeed, our results show that multiple crRNAs act synergistically to produce 1-5% double allele knock-out cells. Surprisingly and unexpectedly, an optimal number of crRNAs (targeting RNAs) produced 4-5% knock-out frequencies and adding further crRNAs did not increase the knock-out frequency. Further, it was surprising and unexpected that 3-4 crRNAs produced far more than additive effects on the knock out frequency, especially when the crRNA sites were located close to each other, e.g., the target sequences for the crRNAs are within 500, 450, 400, 375, 300, 250, 200, 150, 100, or 50 bp of the target cell DNA. This effect of proximity on the frequency of double allele knock-outs was also surprising and unexpected.

When the targeted DNA is cleaved by Cas9 to create double-strand-breaks, the gene of interest may be disrupted by introducing frame-shift insertions or deletions (indels) by non-homologous end joining (NHEJ). When two single-strand cleavage sites are created by the single catalytic site variant Cas9-D10A, the gene of interest may be disrupted by deletion between the cleavages sites. Previously, the Cas9 system has been shown to create targeted gene-editing in multiple mammalian cell types (Mali et al., *Science*, 2013, 339:823-826; Cong, L. et al., *Science*, 2013, 339:819-823). However, since the non-homologous end joining rates are typically low depending on the target site and the cell type, previous Cas9 systems have not been able to select a knock-out cell line null at both alleles in an efficient single step. The present invention describes methods and compositions for the creation of double allele knock-outs in a single step using multiple targeting RNA sites in a gene of interest. In other embodiments, more than one gene is targeted at the same time.

The CRISPR system is applicable to genome modification in many organisms. In nature, CRISPR systems are used by bacteria and archaea to defend against phage and plasmids by RNA-directed degradation of DNA. Exogenous DNA is apparently processed by proteins encoded by some of the CRISPR-associated (cas) genes into small elements (of ~30 bp in length), which are then somehow inserted into the CRISPR locus near the leader sequence. Short segments of foreign DNA, called spacers, are incorporated into the genome between CRISPR repeats, and serve as a 'memory' of past exposures. CRISPR repeats range in size from 24 to 48 base pairs. In Type II CRISPR systems, the Cas9 protein forms a complex with 2 small RNAs sharing a complementary sequence: crRNA and tracrRNA. The crRNA contains a sequence complementary to the DNA spacer sequence and helps to guide the Cas9-RNA complex to the targeted foreign DNA. A single chimeric guiding RNA (gRNA) may be utilized by connecting crRNA and tracrRNA with a hairpin RNA linkage. Cas9 unwinds the DNA duplex and cleaves both strands upon recognition of a target sequence by the crRNA, but a double stranded break results only if the correct protospacer-adjacent motif (PAM) is present at the 3' end. Cas9 can be directed to cleave any sequence with a compatible PAM, by expressing a chimeric gRNA (Mali, P. et al., *Science*, 2013, 339(6121):823-6), or a spacer array together with the tracrRNA required for processing (Cong, L. et al., *Science*, 2013, 339(6121):819-23). Knocking out one of the two Cas9 nuclease domains converts the enzyme into a nickase that causes nicks (breaks in one strand) of nucleic acid, allowing it to unwind. CRISPR is generally described in Richter et al., *Viruses*, 2012, 4:2291-2311; Cong L., supra; and Mali P. et al., supra.

In one embodiment, the gene of interest for targeting is a fucosyltransferase, for example, Fut8, alpha-(1-6)-fucosyltransferase. Fucosyltransferase is an enzyme that transfers an L-fucose sugar from a GDP-fucose (guanosine diphosphate-fucose) donor substrate to an acceptor substrate. The acceptor substrate can be another sugar such as the transfer of a fucose to a core GlcNAc (N-acetylglucosamine) sugar as in the case of N-linked glycosylation, or to a protein, as in the case of O-linked glycosylation produced by 0-fucosyltransferase. In a further embodiment, the targeted gene codes for glutamine synthetase. For example, glutamine synthetase (GS) (EC 6.3.1.2) is an enzyme that plays an essential role in the metabolism of nitrogen by catalyzing the condensation of glutamate and ammonia to form glutamine. In another embodiment, the targeted gene is dihydrofolate reductase (DHFR). Dihydrofolate reductase, or DHFR, is an enzyme that reduces dihydrofolic acid to tetrahydrofolic acid, using NADPH as electron donor, which can be converted to the kinds of tetrahydrofolate cofactors used in 1-carbon transfer chemistry.

In another embodiment, the targeted gene is a sialidase (e.g., NEU2 or NEU3). NEU2 and NEU3 belong to a family of glycohydrolytic enzymes that remove sialic acid residues from glycoproteins and glycolipids. Disrupting NEU2 or NEU3 in antibody-producing cells may prevent the removal of terminal sialic acid from the glycosylated antibody and improve antibody activity and circulating half-life.

In one embodiment, the gene of interest for targeting is a proapoptotic gene, such as BAX, BID, BAK, or BAD. Disrupting a proapoptotic gene in antibody production cells may disrupt apoptotic process and enhance cell survival and antibody production.

CRISPR

Genome-editing nucleases are valuable tools for genetic engineering. The present invention utilizes a sequence-specific nuclease system termed CRISPR (clustered regularly interspaced short palindromic repeats). In vivo, this microbial nuclease system helps defend against invading phages and plasmids. CRISPR loci in microbial hosts contain a combination of CRISPR-associated genes as well as non-coding RNA elements capable of programming the specificity of the CRISPR-mediated nucleic acid cleavage. CRISPR uses genomically encoded RNA arrays to control the cleavage of foreign DNA by a CRISPR-associated (Cas) nuclease. Three types (I-III) of CRISPR systems that utilize Cas variant nucleases have been identified across a wide range of bacterial hosts (Makarova et al., *Nat. Rev. Microbiol.*, 2011, 9(6):467-77; Karvelis et al., *RNA Biol.*, 2013, 10(5):841-51). Each CRISPR locus contains an array of repetitive sequences (direct repeats) interspaced by short stretches of non-repetitive sequences (spacers). The spacer sequence corresponds to a protospacer sequence in the targeted genome, which is typically 20-30 nucleotides followed by an NGG protospacer-adjacent motif (PAM). To utilize the associated Cas nuclease for nucleic acid cleavage, the non-coding CRISPR array is transcribed and cleaved within direct repeats into short crRNAs containing individual spacer sequences, which direct Cas nucleases to the target site (protospacer).

The type II CRISPR utilized in the present invention is well characterized and carries out targeted DNA double-strand break in four sequential steps. First, two non-coding RNA, the pre-crRNA (CRISPR RNAs) array and tracrRNA (trans-activating crRNA), are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer (www.genome-engineering.org/crispr/). At least 12 base pairs (bp) of perfect homology in the spacer sequence, in addition to the PAM, appears to be necessary for CRISPR endonuclease activity (Esvelt and Wang, *Mol. Syst. Biol.*, 2013, 9:641).

Mammalian expression constructs from *Streptococcus pyogenes* CRISPR components, including nuclear-localized Cas9 and processed forms of guide RNAs can be transfected into various cell types to disrupt targeted alleles in a cell population. The CRISPR system is also amenable to multiplexing. Multiple guide sequences can be encoded into a single CRISPR array to enable simultaneous editing of several sites within the mammalian genome.

In addition to initiating targeted gene disruptions, genome editing using CRISPR can also take advantage of the cellular homologous recombination machinery to replace a DNA locus with an engineered donor DNA cassette that contains regions of homology flanking a single-stranded break site. Cong, et al., have disclosed the engineering of two different type II CRISPR systems, which demonstrated that Cas9 nucleases can be directed by short RNAs to induce precise cleavage at endogenous genomic loci in human and mouse cells (*Science*, 2013, 339:819-823). They also reported that Cas9 can be converted into a nicking enzyme to facilitate homology-directed repair with minimal mutagenic activity. Mali, et al., have also disclosed that they engineered the type II bacterial CRISPR system to function with custom guide RNA (gRNA) in human cells (*Science*, 2013, 339:823-826).

Method of Producing Double Allele Knock-Outs

In one embodiment, the present invention comprises a method for producing a double allele knock-out in a eukaryotic cell by providing the cell with a CRISPR system comprising a nuclease and at least two targeting RNAs. In an embodiment, the CRISPR system has 3-4, 3-5, 3-6, 3-7, 3-8, 3-9, or 3-10 targeting RNAs. An example of one application of this method is to produce cells that secrete afucosylated antibodies. The Fut8 gene encodes alpha-(1,6)-fucosyltransferase, an enzyme that catalyzes the transfer of fucose from GDP-fucose to N-linked type complex glycopeptides. Since afucosylated antibodies have enhanced ADCC activity, knocking out Fut8 is desirable in antibody production cells. In one embodiment of the present invention, Chinese hamster Fut8 contains 9 exons, 121,971 nucleotides from starting codon to stop codon. The gene structure of Chinese hamster Fut8 is shown in Table 1.

TABLE 1

| | Exon | | | | | | | | |
|---|---|---|---|---|---|---|---|---|---|
| | 1 | 2 | 3 | 4 | 5 | 6 | 7 | 8 | 9 |
| Sequence | 1-203 | 25955-26069 | 26177-26341 | 48351-48464 | 64540-64776 | 100533-100781 | 102114-102290 | 112809-112961 | 121666-121971 |

The ten protospacer sequences in the first four exons shown in Table 2 may be selected for the construction of expression vectors. In Table 2, the crRNA target "c" refers to the complementary strand and the bold sequences refer to a PAM (protospacer-adjacent motif). These sequences all begin with G to facilitate U6 transcription initiation, and then ~20 nucleotides following by NGG. Multiple crRNA expression vectors may be constructed comprising one of the targeted spacer sequence or multiple spacer sequences.

TABLE 2

| crRNA target | Targeted exon | Target sequence (5'-3') |
|---|---|---|
| T1 (7-30) | Exon 1 | GCATGGACTGGTTCCTGGCGTTGG (SEQ ID NO: 5) |
| T2 (105-127, c) | | GTTCTCTGCTAGAATGGTCAGGG (SEQ ID NO: 6) |
| T3 (131-154, c) | | GCTCCAGCTTTGCAAGAATCTTGG (SEQ ID NO: 7) |
| T4 (182-204) | | GGAGAATGGCTGAGTCTCTCCGG (SEQ ID NO: 8) |
| T5 (25954-25980) | Exon 2 | GAATACCAGAAGGCCCTATTGATCAGG (SEQ ID NO: 9) |
| T6 (26260-26283) | Exon 3 | GAAGAAATTAAAGAAATTAGAAGG (SEQ ID NO: 10) |
| T7 (26293-26315, c) | | GAATTTCATCTGCATGTCTTTGG (SEQ ID NO: 11) |
| T8 (48363-48391) | Exon 4 | GATCTATACTACCTCAGTCAAACAGATGG (SEQ ID NO: 12) |
| T9 (48414-48438) | | GAAGCCAAAGATCTGACAGAGCTGG (SEQ ID NO: 13) |
| T10 (48440-48462, c) | | GCAGATATGTTATTCTCCGCTGG (SEQ ID NO: 14) |

Figure 6A:
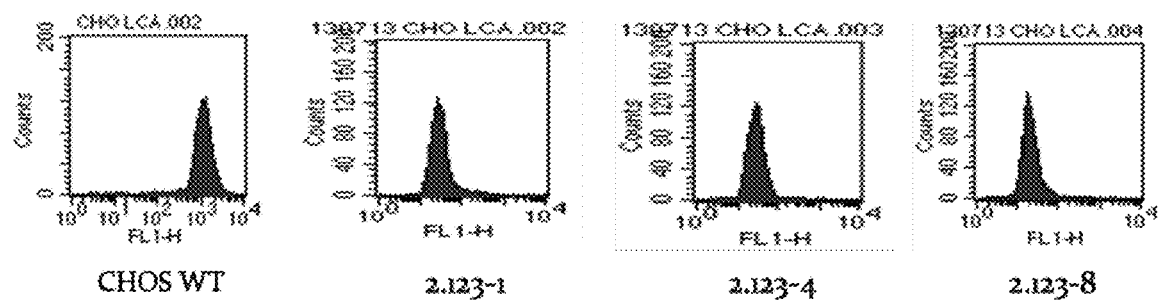
FIG. 6A-C shows LCA-FITC staining of fucose (FIG. 6A); sequence alignments (FIG. 6B: Fut8 Exon 1—SEQ ID NO:1; Mutant 1—SEQ ID NO:2; Mutant 2—SEQ ID NO:3; and Mutant 3—SEQ ID NO:4); and transfection efficiencies for clones isolated from the M2 peak of transfection #5 (three target RNAs) (FIG. 6C). Mutants 1 and 3 are from cell line 2.123-4, and mutant 2 is from cell line 2.123-6. Other mutant cell lines isolated from the M2 peak of transfection #5 are 2.123-1, 2.123-11, 2.123-12, 2.123-13, 2.123-15, 2.123-20, 2.123-23, 2.123-25, and 2.124-6.
Figure 6B:
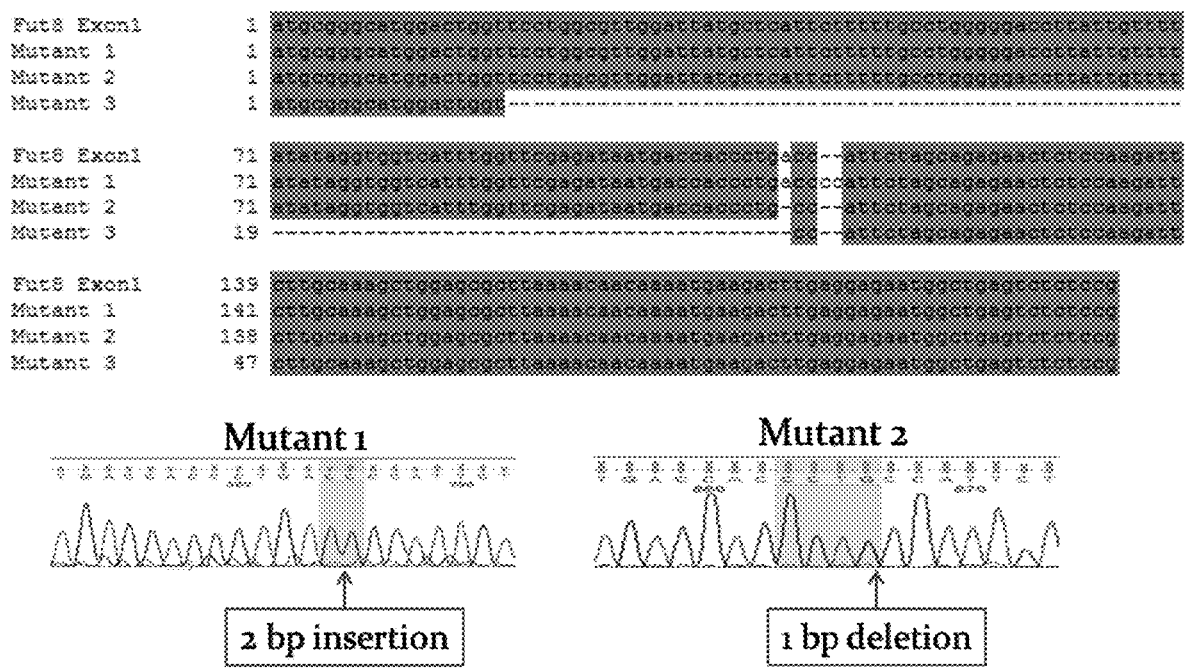

Wild-type CHO cells and an antibody expressing CHO cell line may be used to characterize Fut8 gene knock-out efficiency. Typically, the cells are transfected with at least one mammalian expression vector of Cas9, tracrRNA, and crRNA. After two days of culturing, the cells are continuously monitored for cell surface fucose content by fluorescent labeling with *Lens culinaris* Agglutinin (LCA)-FITC (Vector Laboratories, Burlingame, Calif.) and flow cytometry analysis. Negative binding of LCA-FITC indicates that both alleles of Fut8 have been knocked out. In some embodiments, the Fut8 comprises the modified exon 1 sequence represented by SEQ ID NO: 2, 3 or 4 (as shown in FIG. 6B).

Figure 1C:
Figure 2A:
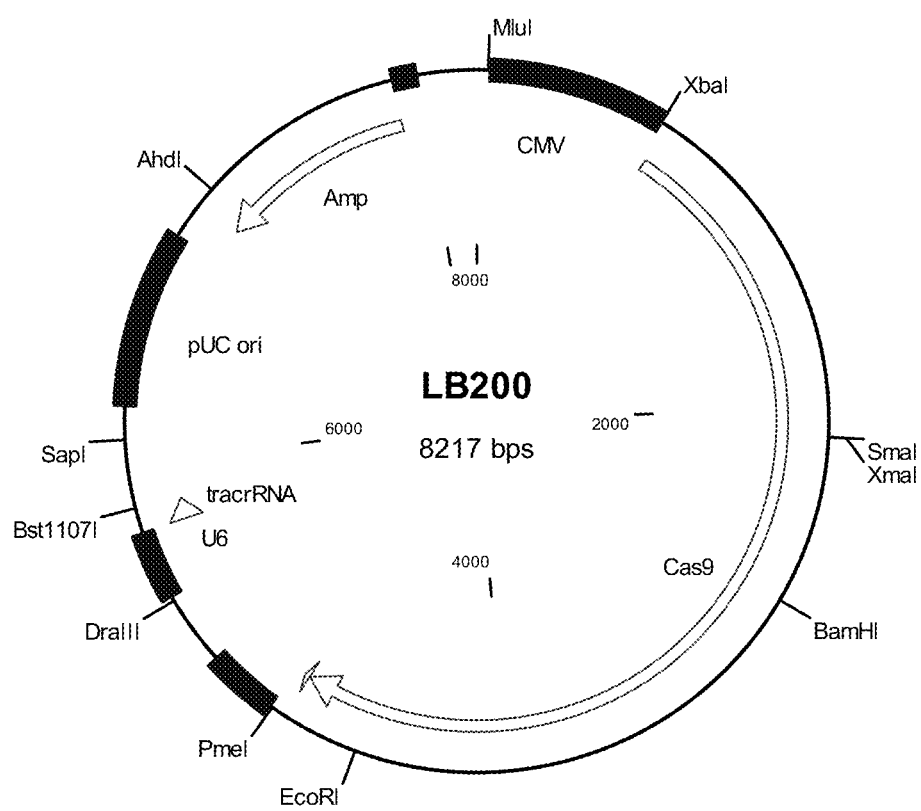
FIG. 2A-B depicts plasmid maps of Cas9 mediated gene targeting system, mammalian cell expression vector LB200 and LB221; Cas9 is transcribed by a CMV promoter; tracrRNA is transcribed by a human U6 promoter.
Figure 2B:
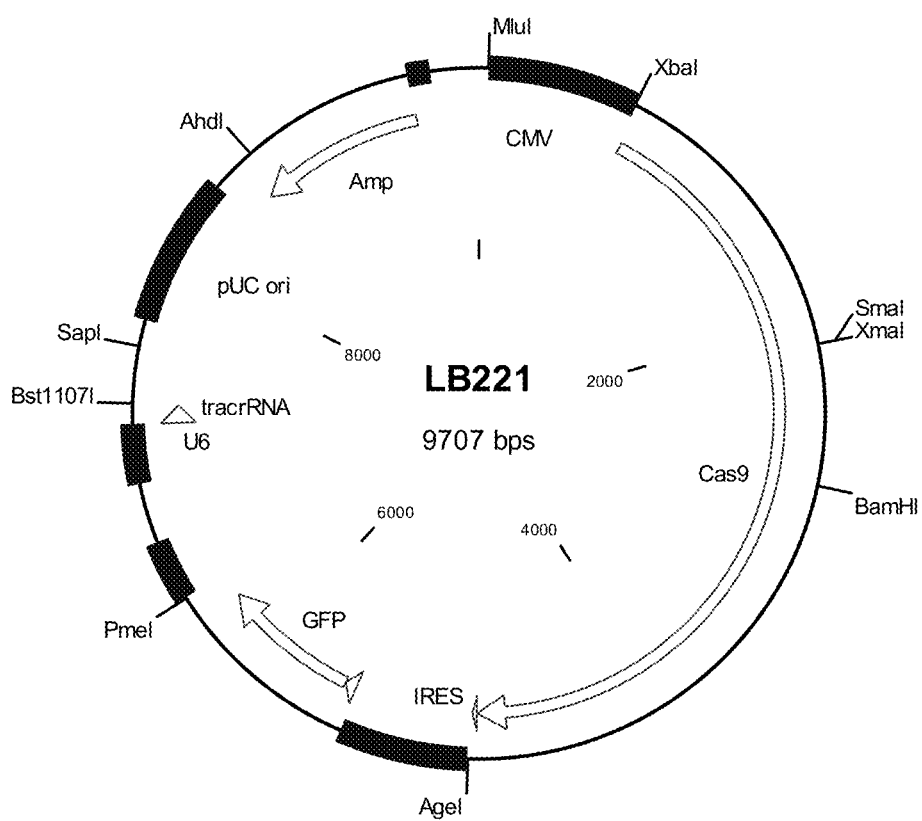
Figure 3:
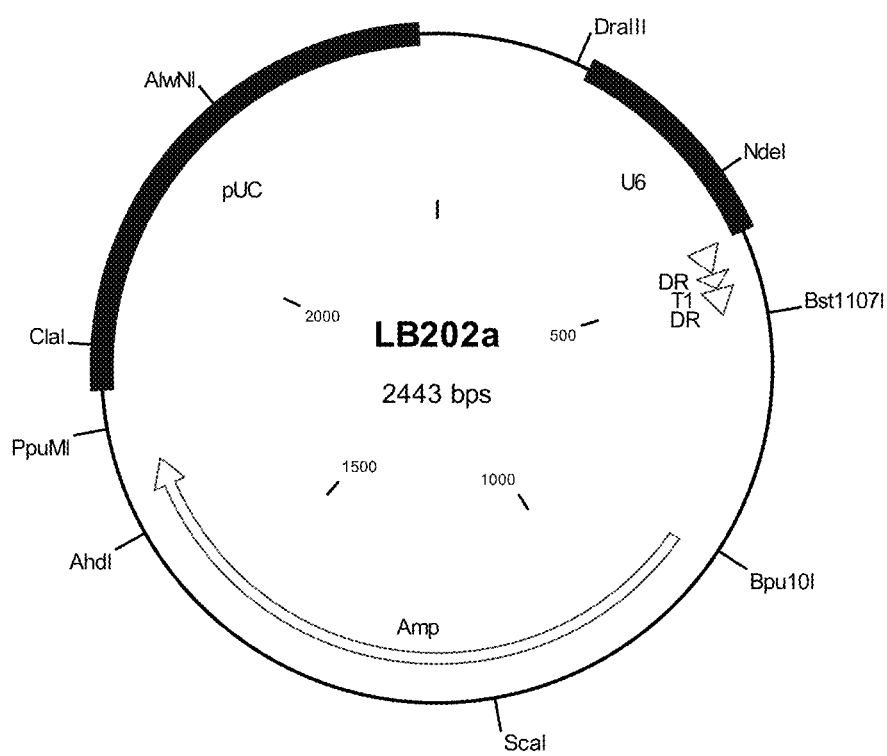
FIG. 3 shows a plasmid map of a Cas9 mediated gene targeting system, mammalian cell expression vector LB202a; crRNA of DR-T1-DR is transcribed by a human U6 promoter.

In another embodiment, the present invention involves a dual-expression vector LB200 containing a Cas9 expression cassette under the control of a CMV promoter and a tracrRNA expression cassette under the control of human U6 promoter (FIG. 2). A separate expression vector or multiple vectors may be used to express crRNA. FIG. 3 shows vector LB202a, the basic structure of a human U6 promoter expressing crRNA, which contains a target sequence (spacer) flanked by direct repeat (DR). The spacer sequence corresponds to a protospacer sequence in the targeted genome, which is typically 20-30 nucleotides followed by protospacer-adjacent motif NGG (PAM). After co-transfection of LB200 and LB202a into the cells of interest, crRNA and tracrRNA form RNA duplex and guide Cas9 to the protospacer sequence in the chromosome. Cas9 then cleaves the DNA at −3 position of PAM. The crRNA may contain multiple spacers following the U6 promoter, for example, 3 spacers are targeted in a crRNA sequence DR-T1-DR-T2-DR-T3-DR (FIG. 1C). Therefore, multiple protospacer sequences may be targeted by Cas9 at the same time.

In certain embodiments, the tracrRNA and the crRNA may be connected by a hairpin RNA linkage. RNA bases include adenine (A), guanine (G), cytosine (C) and uracil (U). RNA molecules are polymers of nucleotides joined to one another by covalent bonds between the phosphate of one nucleotide and the sugar of another. These linkages are called phosphodiester linkages. Although single stranded, RNA is not always linear. It has the ability to fold into complex three dimensional shapes and form hairpin loops. Within these loops, the bases bind to one another: adenine pairs with uracil (A-U) and guanine pairs with cytosine (G-C). Hairpin loops are commonly observed in RNA molecules such as messenger RNA (mRNA) and transfer RNA (tRNA).

Expression vectors herein may contain expression control sequences that are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science,* 1987, 236:237-1245). Exemplary expression control sequences are described in, for example, Goeddel, *Gene Expression Technology: Methods in Enzymology,* 1990, Vol. 185, Academic Press, San Diego, Calif.

Expression of Cas9 may be driven by any eukaryotic promoter, including, but not limited to, a CMV promoter, an EF1α promoter, a SV40 promoter, a RSV promoter, or a PGK promoter. CMV promoters suitable for use in the present invention are available in plasmid form from sources including GSL Biotech LLC (Chicago, Ill.), Promega Corporation (Madison, Wis.), Sigma-Aldrich (St. Louis, Mo.), and Clontech Laboratories (Mountain View, Calif.). Suitable EF1α promoters are available from Clontech Laboratories and Oxford Genetics (Oxfordshire, UK). Suitable SV40 promoters in plasmid form are widely available from sources including Promega Corporation, Invitrogen (Carlsbad, Calif.), and Oxford Genetics. RSV and PGK promoters may be obtained from similar companies.

Expression of RNA may be driven by any RNA polymerase promoter, including, but not limited to, a human U6 promoter, a human H1 promoter, or a human 7SK promoter. Suitable human U6 promoters may be obtained in plasmid form from sources including Invitrogen and Oxford Genetics.

"Targeting RNA" refers to a crRNA that directs Cas9 to the targeted DNA sequence for genome editing. It contains RNA sequence complementary to the protospacer DNA sequence in the gene of interest. Targeting RNA may be connected with full or partial sequence of tracrRNA by a hairpin RNA linkage.

Antibody Production

The method of the present invention and plasmids produced thereby may be used to transfect eukaryotic cells such that those cells then produce antibodies of interest, preferably, therapeutic antibodies. Production and purification of therapeutic antibodies are well known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Particular mammalian host cells for expressing the recombinant antibodies of the invention include Chinese Hamster Ovary (CHO cells), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, in particular, secretion of the antibody into the culture medium in which the host cells are grown. Antibodies can be recovered from the culture medium using standard protein purification methods.

In one embodiment, the methods of the present invention may be used to produce biosimilar antibodies, for example, rituximab antibodies. Biosimilars, also known as follow-on biologics, are biologic medical products whose active drug substance is made by a living organism or derived from a living organism by means of recombinant DNA or controlled gene expression methods. Biosimilars or follow-on biologics are terms used to describe officially approved subsequent versions of innovator biopharmaceutical products made by a different sponsor following patent and exclusivity expiry on the innovator product.

Rituximab (tradename Rituxan™) is a genetically engineered chimeric murine/human monoclonal antibody directed against the CD20 antigen found on the surface of normal and malignant B lymphocytes. The antibody is an IgG1 kappa immunoglobulin containing murine light and heavy-chain variable region sequences and human constant region sequences. Rituximab is composed of two heavy chains of 451 amino acids and two light chains of 213 amino acids. The Fab regions of rituximab bind to the CD20 antigen on B lymphocytes, while the Fc domain recruits antibodies and complement to mediate cell lysis. Rituximab is used in the treatment of CD20-positive non-Hodgkins lymphoma, chronic lymphocytic leukemia, and rheumatoid arthritis.

Trastuzumab (tradename Herceptin™) is a genetically engineered humanized monoclonal antibody directed against the HER2 antigen found on the surface of certain types of breast cancer cells. Trastuzumab is composed of two heavy chains of 451 amino acids and two light chains of 213 amino acids. The Fab regions of trastuzumab bind to the HER2 antigen on breast cancer cells, while the Fc domain recruits antibodies and complement to mediate cell lysis. Trastuzumab is used in the treatment of HER2 overexpressing breast cancers.

The inventions disclosed herein will be better understood from the experimental details which follow. The following examples are offered by way of illustration and not by way of limitation of the inventions as described more fully in the claims which follow thereafter.

EXAMPLES

Example 1: Disruption of Fut8 Gene in CHO Cells by Targeting Single crRNA Sites S. pyogenes tracrRNA (SEQ ID NO:15) was cloned into a mammalian expression vector under the control of a human U6 promoter (SEQ ID NO:16).

```
S. pyogenes tracrRNA
                                              (SEQ ID NO. 15)
ATCTTGTTGGAACCATTCAAAACAGCATAGCAAGTTAAAATAAGGCTAG
TCCGTTATCAACTTGAAAAAGTGGCACCGAGTCGGTGCTTT Human U6 promoter
                                              (SEQ ID NO: 16)
AAGGTCGGGCAGGAAGAGGGCCTATTTCCCATGATTCCTTCATATTTGC

ATATACGATACAAGGCTGTTAGAGAGATAATTAGAATTAATTTGACTGT

AAACACAAAGATATTAGTACAAAATACGTGACGTAGAAAGTAATAATTT

CTTGGGTAGTTTGCAGTTTTAAAATTATGTTTTAAAATGGACTATCATA

TGCTTACCGTAACTTGAAAGTATTTCGATTTCTTGGCTTTATATATCTT

GTGGAAAGGACGAAACACC
```

The tracrRNA expression cassette was synthesized and cloned into vector pcDNA3 (Invitrogen) between restriction sites Dra III and Bst1107 I to give vector LB-tracrRNA. S. pyogenes Cas9 cDNA encoding Cas9 protein (SEQ ID NO:18) was mammalian codon-optimized (SEQ ID NO:17) and fused with a nuclear localization signal (NLS, SEQ ID NO:19 and SEQ ID NO:20).

```
S. pyogenes codon optimized DNA encoding Cas9
                                                     (SEQ ID NO. 17)
    1    ATGGACAAGA AATATTCAAT CGGACTTGAC ATTGGAACAA ACTCTGTCGG CTGGGCCGTC
         M  D  K    K  Y  S    I  G  L  D   I  G  T   N  S  V  G   W  A  V 61    ATTACTGATG AGTACAAAGT GCCATCCAAG AAGTTCAAAG TATTGGGCAA CACAGATCGG
         I  T  D    E  Y  K    V  P  S  K   K  F  K   V  L  G  N   T  D  R 121    CACAGTATCA AAAAAAACCT GATCGGCGCA CTGCTGTTTG ACTCTGGAGA AACCGCTGAG
         H  S  I    K  K  N    L  I  G  A   L  L  F   D  S  G  E   T  A  E 181    GCTACTAGAC TTAAGCGCAC TGCCCGGCGT AGGTACACCA GGAGAAAGAA TCGCATCTGT
         A  T  R    L  K  R    T  A  R  R   R  Y  T   R  R  K  N   R  I  C 241    TATCTGCAGG AGATCTTTAG CAACGAAATG GCTAAGGTTG ACGATAGTTT TTTCCACCGC
         Y  L  Q    E  I  F    S  N  E  M   A  K  V   D  D  S  F   F  H  R 301    CTGGAGGAGA GTTTCCTCGT AGAGGAGGAC AAGAAACACG AGCGTCACCC TATTTTCGGA
         L  E  E    S  F  L    V  E  E  D   K  K  H   E  R  H  P   I  F  G 361    AACATCGTGG ATGAAGTCGC TTACCACGAG AAGTATCCTA CAATTTATCA CTTGCGCAAG
         N  I  V    D  E  V    A  Y  H  E   K  Y  P   T  I  Y  H   L  R  K 421    AAACTCGTGG ATAGCACAGA CAAAGCTGAC CTGCGCCTTA TCTATCTGGC ACTGGCACAT
         K  L  V    D  S  T    D  K  A  D   L  R  L   I  Y  L  A   L  A  H 481    ATGATAAAGT TTCGCGGGCA TTTCCTTATT GAGGGAGATT TGAATCCCGA TAACAGTGAC
         M  I  K    F  R  G    H  F  L  I   E  G  D   L  N  P  D   N  S  D 541    GTGGATAAAC TTTTCATACA ATTGGTCCAG ACCTATAATC AACTCTTTGA AGAGAATCCA
         V  D  K    L  F  I    Q  L  V  Q   T  Y  N   Q  L  F  E   E  N  P 601    ATCAACGCAT CTGGTGTGGA CGCTAAGGCC ATTCTCAGTG CCCGGCTGTC AAAATCTAGG
         I  N  A    S  G  V    D  A  K  A   I  L  S   A  R  L  S   K  S  R 661    CGCCTTGAGA ATCTGATTGC ACAGCTGCCC GGGGAAAAGA AGAACGGCTT GTTTGGAAAT
         R  L  E    N  L  I    A  Q  L  P   G  E  K   K  N  G  L   F  G  N 721    CTGATCGCTC TGTCTCTGGG TCTCACACCT AATTTCAAGT CAAATTTCGA CCTGGCCGAG
         L  I  A    L  S  L    G  L  T  P   N  F  K   S  N  F  D   L  A  E
```

```
-continued

781   GATGCAAAGC TTCAGCTTAG CAAAGATACC TACGATGATG ACCTCGACAA TCTTCTCGCC
        D  A  K   L  Q  L   S  K  D  T   Y  D  D   D  L  D   N  L  L  A

841   CAGATCGGCG ACCAATATGC TGACCTGTTC CTGGCCGCTA AGAATCTGTC TGATGCCATC
        Q  I  G   D  Q  Y   A  D  L  F   L  A  A   K  N  L   S  D  A  I

901   CTGCTTTCTG ATATCCTGCG CGTCAATACC GAATAACCA AGGCACCACT TTCTGCTTCC
        L  L  S   D  I  L   R  V  N  T   E  I  T   K  A  P   L  S  A  S

961   ATGATTAAAA GGTACGACGA GCATCACCAA GATCTCACTC TCCTTAAGGC CCTTGTGCGT
        M  I  K   R  Y  D   E  H  H  Q   D  L  T   L  L  K   A  L  V  R

1021   CAGCAACTGC CCGAAAAGTA CAAAGAAATC TTCTTTGACC AGTCTAAGAA TGGGTACGCC
        Q  Q  L   P  E  K   Y  K  E  I   F  F  D   Q  S  K   N  G  Y  A

1081   GGCTACATCG ATGGAGGCGC ATCCCAGGAA GAATTTTATA AGTTCATTAA GCCCATACTG
        G  Y  I   D  G  G   A  S  Q  E   E  F  Y   K  F  I   K  P  I  L

1141   GAAAAGATGG ACGGCACTGA GGAACTGCTT GTCAAGCTGA ACAGAGAAGA TCTTCTGCGC
        E  K  M   D  G  T   E  E  L  L   V  K  L   N  R  E   D  L  L  R

1201   AAACAGCGTA CCTTCGATAA TGGTTCTATT CCACACCAAA TTCATCTGGG AGAGCTCCAC
        K  Q  R   T  F  D   N  G  S  I   P  H  Q   I  H  L   G  E  L  H

1261   GCCATTCTCC GGAGACAAGA GGACTTTTAT CCATTCCTGA AGGATAATCG CGAGAAGATC
        A  I  L   R  R  Q   E  D  F  Y   P  F  L   K  D  N   R  E  K  I

1321   GAAAAGATTC TCACATTTCG GATTCCATAC TACGTTGGCC CCCTTGCCCG AGGTAATAGC
        E  K  I   L  T  F   R  I  P  Y   Y  V  G   P  L  A   R  G  N  S

1381   CGTTTTGCTT GGATGACCAG GAAGAGTGAG GAAACCATTA CCCCTTGAA CTTTGAAGAA
        R  F  A   W  M  T   R  K  S  E   E  T  I   P  W  N   F  E  E

1441   GTGGTAGATA AGGGAGCCTC CGCACAAAGC TTTATTGAGC GAATGACTAA TTTCGATAAG
        V  V  D   K  G  A   S  A  Q  S   F  I  E   R  M  T   N  F  D  K

1501   AATCTGCCAA ACGAAAAAGT CTTGCCTAAA CACTCCCTGC TGTACGAGTA TTTCACAGTG
        N  L  P   N  E  K   V  L  P  K   H  S  L   L  Y  E   Y  F  T  V

1561   TATAACGAGT TGACAAAAGT CAAGTATGTT ACTGAGGGCA TGCGAAAACC CGCTTTCCTG
        Y  N  E   L  T  K   V  K  Y  V   T  E  G   M  R  K   P  A  F  L

1621   TCCGGTGAAC AGAAAAAAGC CATTGTCGAC CTGCTCTTTA AAACTAACCG TAAGGTCACC
        S  G  E   Q  K  K   A  I  V  D   L  L  F   K  T  N   R  K  V  T

1681   GTCAAACAAC TTAAGGAAGA CTATTTTAAG AAAATCGAGT GCTTTGACTC CGTTGAGATT
        V  K  Q   L  K  E   D  Y  F  K   K  I  E   C  F  D   S  V  E  I

1741   TCCGGAGTAG AAGATCGATT CAACGCCAGT CTGGGTACAT ATCACGACCT CCTGAAGATA
        S  G  V   E  D  R   F  N  A  S   L  G  T   Y  H  D   L  L  K  I

1801   ATCAAAGACA AGGATTTTCT GGATAATGAG GAGAATGAGG ACATACTGGA GGACATTGTC
        I  K  D   K  D  F   L  D  N  E   E  N  E   D  I  L   E  D  I  V

1861   CTGACCTTGA CCTTGTTCGA AGACCGGGAA ATGATTGAAG AGAGGCTGAA AACCTACGCC
        L  T  L   T  L  F   E  D  R  E   M  I  E   E  R  L   K  T  Y  A

1921   CACCTGTTCG ACGATAAGGT TATGAAGCAA CTGAAACGTA GGAGGTACAC TGGGTGGGGC
        H  L  F   D  D  K   V  M  K  Q   L  K  R   R  R  Y   T  G  W  G

1981   CGACTTTCTC GTAAGCTTAT TAACGGAATT AGAGATAAGC AGTCTGGTAA GACCATTCTC
        R  L  S   R  K  L   I  N  G  I   R  D  K   Q  S  G   K  T  I  L

2041   GACTTCCTGA AAAGCGATGG CTTTGCTAAC CGTAACTTTA TGCAGCTGAT TCACGACGAT
        D  F  L   K  S  D   G  F  A  N   R  N  F   M  Q  L   I  H  D  D

2101   TCTCTGACAT TCAAAGAAGA TATCCAGAAA GCTCAAGTCT CTGGTCAGGG CGACAGCCTG
        S  L  T   F  K  E   D  I  Q  K   A  Q  V   S  G  Q   G  D  S  L

2161   CACGAGCACA TTGCAAACCT GGCCGGCAGC CCAGCTATCA AGAAGGGAAT ACTTCAAACA
        H  E  H   I  A  N   L  A  G  S   P  A  I   K  K  G   I  L  Q  T

2221   GTGAAGGTGG TAGACGAGCT GGTGAAGGTC ATGGGTCGCC ACAAGCCAGA AAACATAGTA
        V  K  V   V  D  E   L  V  K  V   M  G  R   H  K  P   E  N  I  V

2281   ATCGAGATGG CACGTGAAAA CCAGACAACC CAGAAGGGGC AGAAGAATTC TAGAGAGCGG
        I  E  M   A  R  E   N  Q  T  T   Q  K  G   Q  K  N   S  R  E  R

2341   ATGAAAAGAA TTGAGGAAGG GATCAAGGAA CTGGGCTCTC AGATCCTCAA GGAGCACCCA
        M  K  R   I  E  E   G  I  K  E   L  G  S   Q  I  L   K  E  H  P
```

```
-continued
2401  GTAGAGAATA CACAGCTCCA AAATGAAAAA CTGTACTTGT ATTACCTGCA AAACGGCAGG
       V  E  N    T  Q  L    Q  N  E  K   L  Y  L    Y  Y  L    Q  N  G  R 2461  GACATGTACG TCGACCAGGA ACTGGACATT AATCGCCTGA GTGATTATGA CGTCGACCAT
       D  M  Y    V  D  Q   E  L  D  I   N  R  L    S  D  Y    D  V  D  H 2521  ATCGTCCCTC AGTCCTTCCT GAAAGATGAT AGCATCGACA ACAAAGTCCT CACTCGGTCC
       I  V  P    Q  S  F    L  K  D  D   S  I  D   N  K  V    L  T  R  S 2581  GACAAAAACC GTGGCAAGAG CGACAATGTC CCTTCTGAGG AAGTTGTGAA AAAGATGAAG
       D  K  N    R  G  K    S  D  N  V   P  S  E    E  V  V    K  K  M  K 2641  AATTATTGGC GTCAGCTCCT GAATGCAAAG TTGATCACTC AGAGGAAATT CGACAATCTC
       N  Y  W    R  Q  L    L  N  A  K   L  I  T    Q  R  K    F  D  N  L 2701  ACTAAGGCTG AGCGAGGAGG GCTGTCCGAG CTGGACAAAG CCGGATTTAT CAAACGTCAA
       T  K  A    E  R  G    G  L  S  E   L  D  K    A  G  F    I  K  R  Q 2761  CTCGTTGAGA CTCGGCAGAT CACTAAGCAC GTCGCTCAAA TCCTTGATTC CAGAATGAAT
       L  V  E    T  R  Q    I  T  K  H   V  A  Q    I  L  D    S  R  M  N 2821  ACCAAGTACG ATGAAAACGA TAAGTTGATC CGCGAGGTGA AAGTCATTAC ACTGAAGTCT
       T  K  Y    D  E  N    D  K  L  I   R  E  V    K  V  I    T  L  K  S 2881  AAGCTCGTGT CTGATTTTCG CAAGGACTTC CAATTCTATA AAGTGAGGGA GATCAACAAT
       K  L  V    S  D  F    R  K  D  F   Q  F  Y    K  V  R    E  I  N  N 2941  TATCACCACG CCCACGACGC TTATCTCAAT GCTGTGGTGG GCACTGCCCT GATCAAGAAA
       Y  H  H    A  H  D    A  Y  L  N   A  V  V    G  T  A    L  I  K  K 3001  TATCCCAAAC TGGAGTCAGA GTTTGTGTAT GGAGATTACA AAGTGTACGA TGTGAGGAAG
       Y  P  K    L  E  S    E  F  V  Y   G  D  Y    K  V  Y    D  V  R  K 3061  ATGATCGCCA AGAGCGAGCA GGAGATCGGA AAAGCAACAG CCAAGTACTT CTTTTACAGC
       M  I  A    K  S  E    Q  E  I  G   K  A  T    A  K  Y    F  F  Y  S 3121  AATATCATGA ATTTCTTTAA GACCGAGATC ACCTTGGCCA ATGGTGAGAT CCGAAAACGC
       N  I  M    N  F  F    K  T  E  I   T  L  A    N  G  E    I  R  K  R 3181  CCTCTGATAG AGACTAATGG CGAAACTGGT GAGATTGTTT GGGACAAGGG AAGAGATTTC
       P  L  I    E  T  N    G  E  T  G   E  I  V    W  D  K    G  R  D  F 3241  GCAACTGTGA GGAAGGTCCT GTCTATGCCC CAGGTGAATA TCGTTAAAAA GACCGAGGTG
       A  T  V    R  K  V    L  S  M  P   Q  V  N    I  V  K    K  T  E  V 3301  CAGACTGGTG GCTTCAGTAA GGAGTCTATC CTGCCTAAGC GCAACAGCGA CAAACTGATT
       Q  T  G    G  F  S    K  E  S  I   L  P  K    R  N  S    D  K  L  I 3361  GCACGAAAGA AGGACTGGGA CCCCAAGAAA TACGGAGGGT TCGACAGCCC TACCGTGGCT
       A  R  K    K  D  W    D  P  K  K   Y  G  G    F  D  S    P  T  V  A 3421  TACAGCGTGC TTGTGGTCGC AAAGGTGGAG AAGGGGAAAT CTAAGAAGCT GAAAAGTGTG
       Y  S  V    L  V  V    A  K  V  E   K  G  K    S  K  K    L  K  S  V 3481  AAAGAGCTGC TGGGCATTAC CATTATGGAA CGGAGTTCTT TCGAGAAGAA CCCCATCGAT
       K  E  L    L  G  I    T  I  M  E   R  S  S    F  E  K    N  P  I  D 3541  TTTCTGGAAG CCAAGGGCTA TAAGGAAGTT AAAAAGGACT TGATTATCAA GCTGCCTAAG
       F  L  E    A  K  G    Y  K  E  V   K  K  D    L  I  I    K  L  P  K 3601  TATAGTTTGT TCGAACTTGA AAACGGTAGA AAAAGGATGC TCGCCTCCGC AGGTGAGCTG
       Y  S  L    F  E  L    E  N  G  R   K  R  M    L  A  S    A  G  E  L 3661  CAGAAGGGAA ACGAATTGGC TCTCCCATCC AAATACGTGA ACTTCTTGTA CCTGGCCAGC
       Q  K  G    N  E  L    A  L  P  S   K  Y  V    N  F  L    Y  L  A  S 3721  CATTACGAAA AACTCAAAGG CTCCCCAGAG GACAACGAAC AGAAGCAGCT GTTTGTGGAA
       H  Y  E    K  L  K    G  S  P  E   D  N  E    Q  K  Q    L  F  V  E 3781  CAACATAAAC ATTACTTGGA CGAAATAATC GAGCAGATCA GCGAGTTTTC CAAGAGAGTT
       Q  H  K    H  Y  L    D  E  I  I   E  Q  I    S  E  F    S  K  R  V 3841  ATCCTGGCCG ATGCAAACCT CGATAAGGTC CTTTCCGCCT ACAACAAGCA CAGAGACAAA
       I  L  A    D  A  N    L  D  K  V   L  S  A    Y  N  K    H  R  D  K 3901  CCAATCCGGG AGCAGGCCGA GAATATTATC CACCTGTTCA CCCTGACAAA CCTTGGAGCA
       P  I  R    E  Q  A    E  N  I  I   H  L  F    T  L  T    N  L  G  A 3961  CCTGCTGCAT TCAAATATTT CGATACTACA ATCGATCGAA AGCGCTACAC AAGTACCAAG
       P  A  A    F  K  Y    F  D  T  T   I  D  R    K  R  Y    T  S  T  K
```

```
4021    GAGGTGCTGG ACGCCACTCT GATCCATCAG TCCATAACTG GACTGTATGA AACTCGTATC
          E  V  L   D  A  T   L  I  H  Q   S  I  T     G  L  Y    E  T  R  I

4081    GATCTGAGCC AGTTGGGGGG AGATTCTCGG GCAGAT
          D  L  S   Q  L  G   G  D  S  R   A  D nuclear localization signal
        CCC AAG AAG AAG AGG AAG GTG (SEQ ID NO: 19)
         P   K   K   K   R   K   V  (SEQ ID NO: 20)
```

The Cas9 cDNA was synthesized and cloned into vector LB-tracrRNA between restriction sites Xba I and Pme I to give vector LB200. Expression of Cas9 was driven by a CMV promoter. The plasmid map of LB200 is shown in FIG. 2. A single mutation D10A of Cas9 was introduced by site-specific mutagenesis in LB200 to give vector LB201. Vector LB202a, LB202b, and LB202c (Table 3) were constructed to express crRNA driven by a human U6 promoter targeting single protospacer sequence T1, T2, or T3 in the hamster Fut8 gene, respectively. The targeting protospacers were flanked by the CRISPR direct repeat (DR; SEQ ID NO:21).

```
         S. pyogenes CRISPR direct repeat
                                    (SEQ ID NO: 21)
         GTTTTAGAGCTATGCTGTTTTGAATGGTCCCAAAAC
```

The expression cassettes were synthesized and cloned in vector pIDT-Smart (Integrated DNA Technologies). The plasmid map of LB202a is shown in FIG. 3. All plasmids carry an ampicillin resistant gene for bacterial propagation.

TABLE 3

| Plasmid | crRNA structure |
|---|---|
| LB202a | DR-T1-DR |
| LB202b | DR-T2-DR |
| LB202c | DR-T3-DR |
| LB203 | DR-T1-DR-T2-DR |
| LB204 | DR-T1-DR-T2-DR-T3-DR |
| LB205 | DR-T1-DR-T2-DR-T3-DR-T4-DR |
| LB206 | DR-T5-DR-T6-DR-T7-DR |
| LB207 | DR-T8-DR-T9-DR-T10-DR |

Figure 4A:
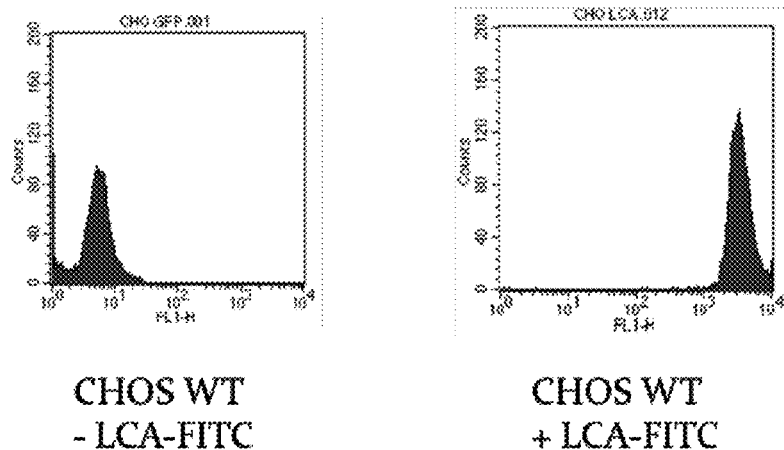
FIG. 4A-B shows LCA-FITC staining of fucose on CHOS cells before and after introduction of CRISPR systems targeting Fut8.
Figure 4B:
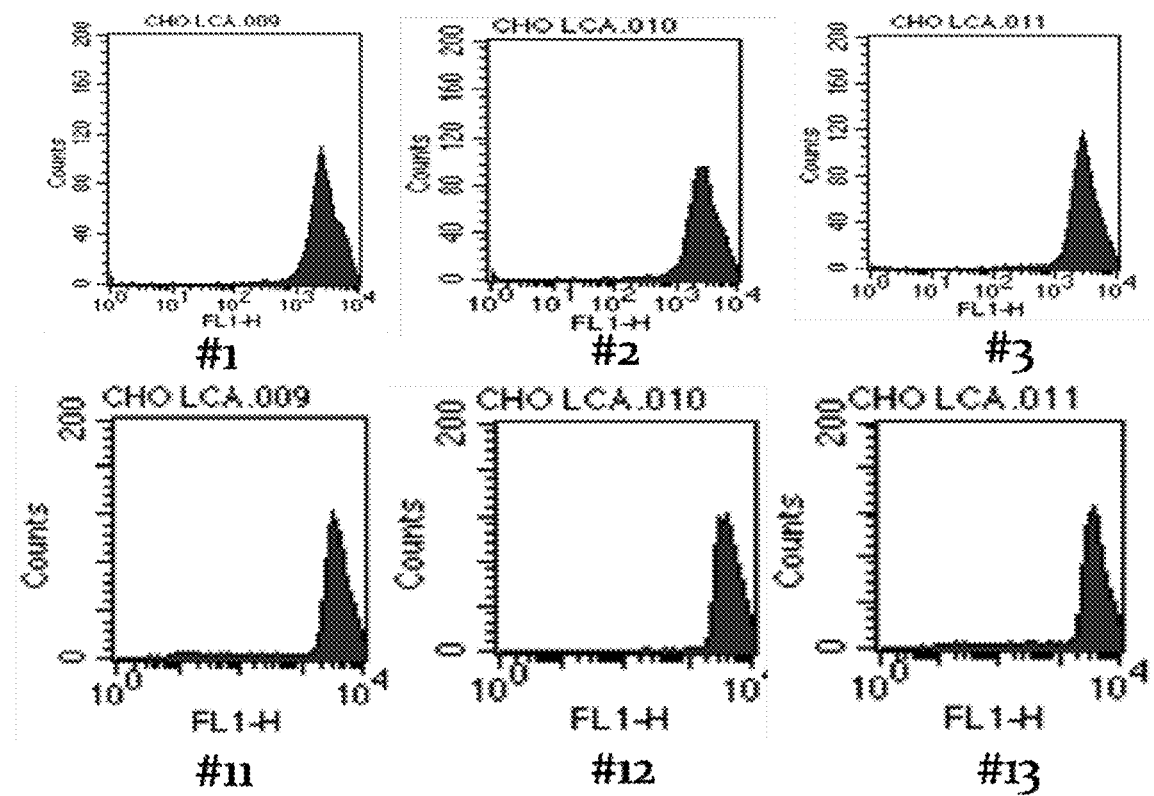

Fucose on the CHOS cell surface (Invitrogen, Carlsbad, Calif.) can be readily detected by staining with 5 μg/ml of fluorescent Lens culinaris Agglutinin (LCA-FITC, Vector Laboratories), and then subjected to flow cytometric analysis (FIG. 4a). Cells with Fut8 knocked out lack surface fucose and hence exhibit negative staining of LCA-FITC. To test Fut8 genome editing CRISPR vectors, $1 \times 10^6$ CHOS cells were co-transfected with two plasmids, one from LB200 and LB201, the other from LB202a, LB202b, and LB202c, totaling six conditions (#1-3, #11-13, Table 4). The transfection was carried out using Neon Electroporation System (Invitrogen). One week after transfection, the cells were stained with LCA-FITC, and then subjected to flow cytometric analysis. None of the transfectant cells showed detectable fucose negative populations, indicating the efficiency of biallelic Fut8 knock out by targeting of one CRISPR sequence was negligible (FIG. 4b).

TABLE 4

| Transfection condition | Plasmid 1 | Plasmid 2 | Targeting sites |
|---|---|---|---|
| 1 | LB200 | LB202a | T1 |
| 2 | | LB202b | T2 |

TABLE 4-continued

| Transfection condition | Plasmid 1 | Plasmid 2 | Targeting sites |
|---|---|---|---|
| 3 | | LB202c | T3 |
| 4 | | LB203 | T1-2 |
| 5 | | LB204 | T1-3 |
| 6 | | LB205 | T1-4 |
| 7 | | LB206 | T5-7 |
| 8 | | LB207 | T8-10 |
| 9 | | LB205 + LB206 | T1-7 |
| 10 | | LB205 + LB206 + LB207 | T1-10 |
| 11 | LB201 | LB202a | T1 |
| 12 | | LB202b | T2 |
| 13 | | LB202c | T3 |
| 14 | | LB203 | T1-2 |
| 15 | | LB204 | T1-3 |
| 16 | | LB205 | T1-4 |
| 17 | | LB206 | T5-7 |
| 18 | | LB207 | T8-10 |
| 19 | | LB205 + LB206 | T1-7 |
| 20 | | LB205 + LB206 + LB207 | T1-10 |

Example 2: Disruption of Fut8 Gene in CHO Cells by Targeting Multiple crRNA Sites Mammalian expression vectors LB203-207 (Table 3) were constructed to express crRNA targeting multiple target sequences T1-T10 in the hamster Fut8 gene. All vectors utilized human U6 promoter to express a crRNA array similar to that in FIG. 1C.

$1 \times 10^6$ CHOS cells were co-transfected with 2-4 plasmids shown in Table 4 (condition #4-10, #14-20). One week after transfection, the cells were stained with LCA-FITC, and then subjected to flow cytometric analysis to determine binding of LCA to cell surface fucose.

Figure 5A:
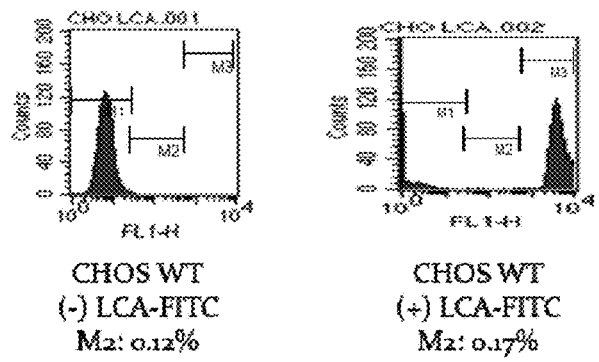
FIG. 5A-C shows LCA-FITC staining of fucose on CHOS cells before and after introduction of CRISPR systems targeting Fut8 with 1-10 targeting RNAs or crRNAs.
Figure 5B:
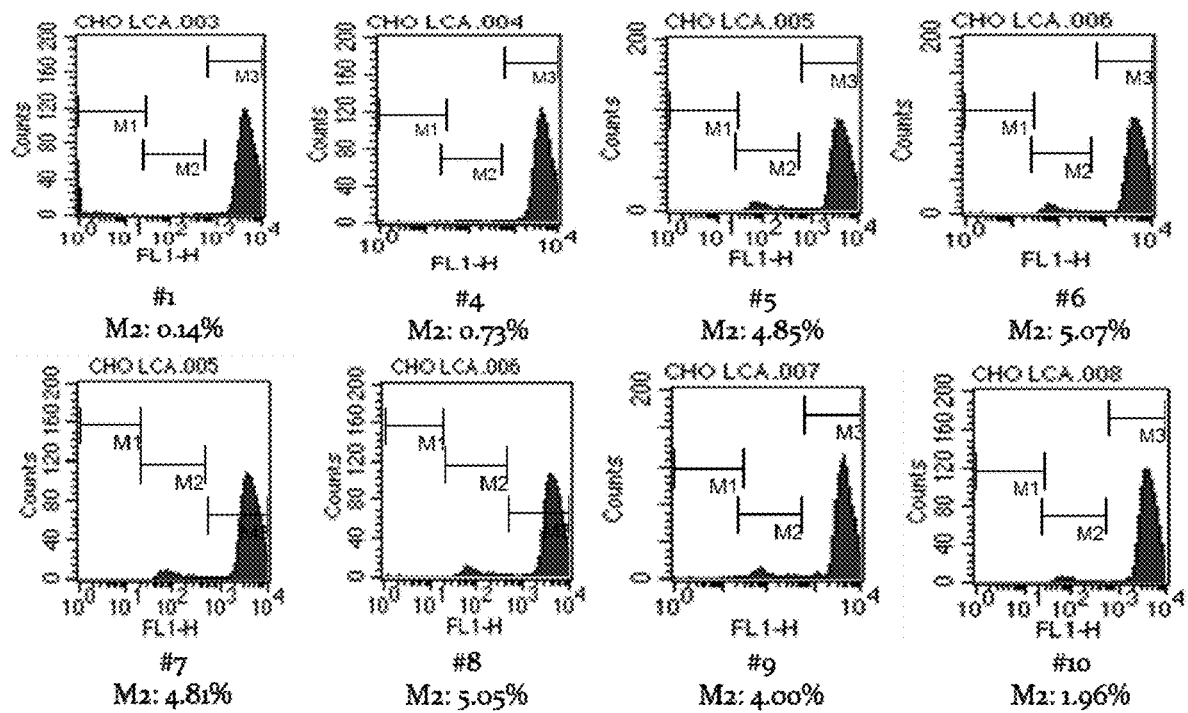
Figure 5C:
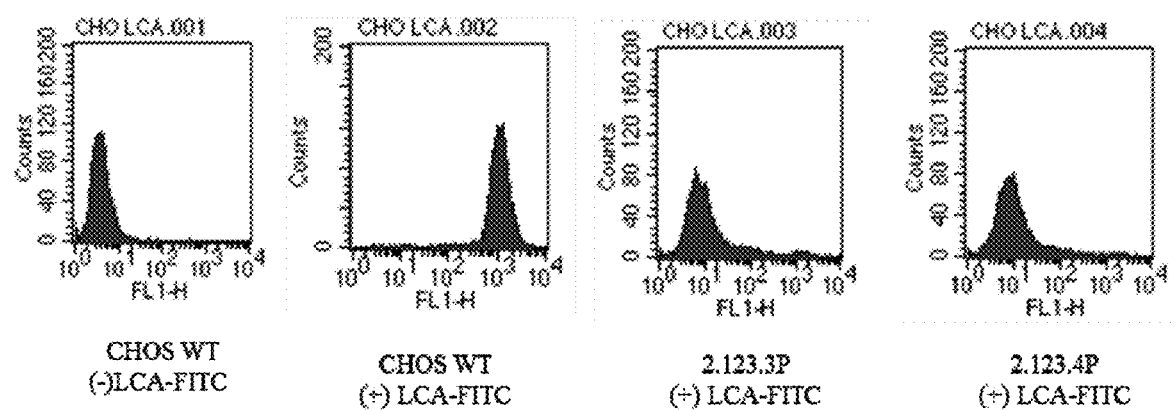

Wild type CHO-S cells exhibited strong staining of LCA on the cell surface (FIG. 5a). Most of the cells resided in the M3 peak with a strong fluorescence signal intensity. Transfection #1 (one CRISPR targeting sequence) showed similar results as the control cells without transfection. The M2 peak representing background staining of LCA-FICT was 0.14%, similar to that of the negative control cells. Transfection #4 (two CRISPR targeting sequences) showed enhanced M2 peak (0.73%) indicating a small percentage of cells lacked surface fucose. In transfections #5-8 (3, 4, 3 or 3 CRISPR targeting sequences), ~5% of the cells lost cell surface fucose indicating much enhanced biallelic genome editing. In transfection #9-10, 7 or 10 CRISPR targeting sequences were utilized by co-transfection of 3 or 4 plasmids. 2-4% of the cells lost cell surface fucose. The slight decrease of genome editing efficiency was consistent with the decreased co-transfection efficiency. $10^3$ Cells in the M2 peak of transfection #5 and #6 were sorted into pools 2.123.3P and 2.123.4P, respectively. Their lack of LCA staining was confirmed after staining with 1 μg/ml of LCA-FITC (FIG. 5c). The results from these transfections are shown in Table 5.

TABLE 5

| Cells | LCA-FITC | Co-transfection Plasmids | CRISPR Targets | LCA-FITC negative ($M_2$, %) |
|---|---|---|---|---|
| wt CHO-S | − | 0 | 0 | 0.12 |
| wt CHO-S | + | 0 | 0 | 0.17 |
| Transfection #1 | + | 2 | 1 | 0.14 |
| Transfection #4 | + | 2 | 2 | 0.73 |
| Transfection #5 | + | 2 | 3 (T1-3) | 4.85 |
| Transfection #6 | + | 2 | 4 (T1-4) | 5.07 |
| Transfection #7 | + | 2 | 3 (T5-7) | 4.81 |
| Transfection #8 | + | 2 | 3 (T8-10) | 5.05 |
| Transfection #9 | + | 3 | 7 (T1-7) | 4.00 |
| Transfection #10 | + | 4 | 10 (T1-10) | 1.96 |

Cells transfected with 3-4 CRISPR targets had the highest frequency of double allele knock-outs of Fut8. Cells transfected with 2 CRISPR targets also produced double allele knock-outs, whereas cells transfected with a single CRISPR target did not produce double allele knock-outs detectable over the background. The combination of 3-4 CRISPR targets together in a cell, surprisingly and unexpectedly, produce a synergistic effect in which the frequency of double allele knock-outs was far greater than the predicted rate from the additive effect of the combined CRISPR targets. It was also surprising that cells transformed with 3-4 CRISPR targets had higher frequency of double allele knock-outs than cells transformed with 7 or 10 CRISPR targets. There was a surprising and unexpected distance effect as closer spacing of the multiple CRISPR targets increased the frequency of double allele knock-outs.

Transfection #14-20 exhibited similar LCA-FITC staining profiles as that of transfection #11-13 as shown in FIG. 4b, suggesting Cas9-D10A had a lower activity than wild-type Cas9 and was not suitable for bi-allelic genome editing.

Example 3: Isolation of Fut8 Knock-Out CHO Cells

Cells in the M2 peak of transfection #5 were sorted into 96-well plates as single cells. After colonies grew out in 2 weeks, 11 clones exhibiting a similar growth profile as the wild-type CHOS cells were picked and expanded into shake flasks and cryopreserved. These clones were confirmed to be negative on LCA-FITC staining and to contain biallelic frame-shift mutations in the Fut8 gene by PCR and sequencing. The LCA staining data of 3 clones are shown in FIG. 6A. Sequence alignment of the exon 1 for 3 modified Fut8 alleles are shown in FIG. 6B (SEQ ID NOS:1-4), indicating frame-shift mutations of 2 bp insertion, 1 bp deletion, and 91 bp deletion. Indels in the first 2 mutants occurred at the cleavage site of the protospace T2. The deletion in the 3rd mutant occurred between the protospacers T1 and T2.

Figure 6C:
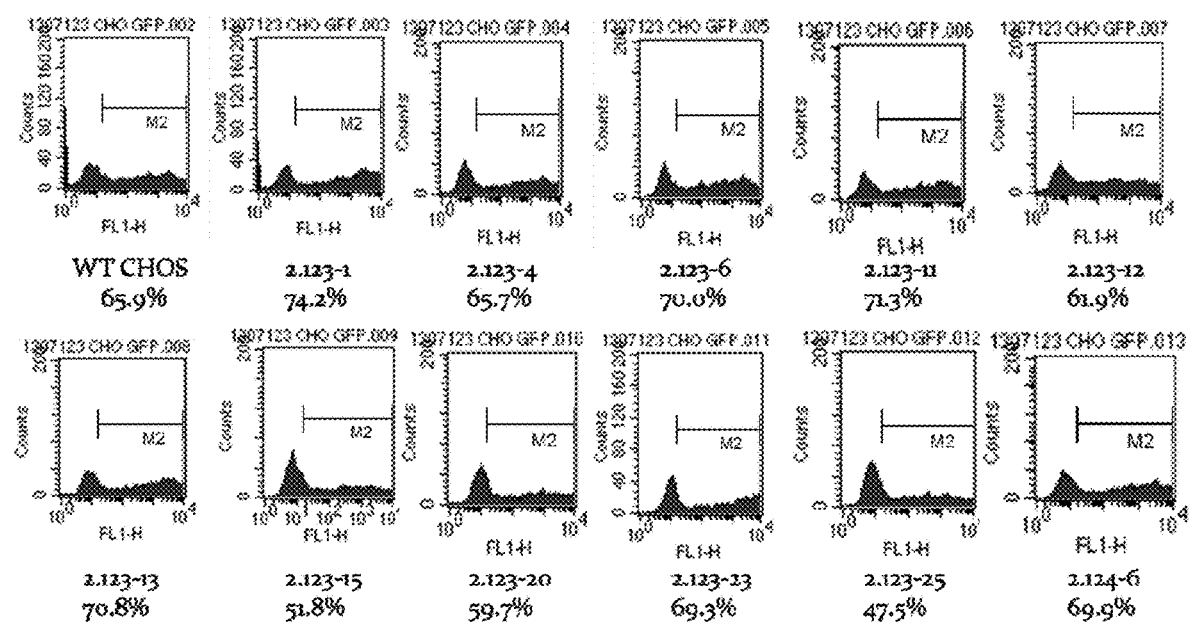

The 11 Fut8−/− CHO clones were tested for transfection efficiency using a GFP expression vector. $1 \times 10^6$ cells were transfected with 10 μg of DNA using a Neon Electroporation System and the percentage of GFP positive cells were characterized by flowmetric analysis after 2 days. Most of the clones exhibited similar transfection efficiency as the wild-type CHOS cells (FIG. 6C).

The 11 Fut8−/− CHO clones were also tested for antibody production after transient transfection. Rituximab was used as the model antibody. $1 \times 10^6$ cells were co-transfected with 5 μg each of the rituximab heavy and light chain expression vectors using Neon Electroporation System. The antibody concentrations in the culture media were determined by Elisa after 2 days (Table 6). Clones 2.123-4, -6 and -13 exhibited similar antibody expression levels as the wild-type CHOS cells.

TABLE 6

| Cells | Ab (ug/ml) |
|---|---|
| WT CHOS | 0.58 |
| 2.123-1 | 0.03 |
| 2.123-4 | 0.51 |
| 2.123-6 | 0.52 |
| 2.123-11 | 0.32 |
| 2.123-12 | 0.06 |
| 2.123-13 | 0.49 |
| 2.123-15 | 0.32 |
| 2.123-20 | 0.14 |
| 2.123-23 | 0.32 |
| 2.123-25 | 0.20 |
| 2.124-6 | 0.17 |

Example 4: Production and Characterization of Afucoslylated Antibodies

Nucleotide sequences coding biosimilar antibody rituximab heavy and light chain sequences were cloned into mammalian expression vectors under hEF1α promoter. The rituximab heavy chain protein sequence and coding nucleotide sequence including introns are provided as SEQ ID NO:22 and SEQ ID NO:23, respectively. The rituximab light chain protein sequence and coding nucleotide sequence are provided as SEQ ID NO:24 and SEQ ID NO:25, respectively.

Nucleotide sequences coding biosimilar antibody trastuzumab heavy and light chain sequences were cloned into mammalian expression vectors so the hEF1α promoter controlled expression. The trastuzumab heavy chain protein sequence and coding nucleotide sequence including introns are provided as SEQ ID NO:26 and SEQ ID NO:27, respectively. The trastuzumab light chain protein sequence and coding nucleotide sequence are shown in SEQ ID NO:28 and SEQ ID NO:29, respectively.

The rituximab and trastuzumab expression plasmids were used to transfect wild-type CHOS cells, or 2 different Fut8−/− CHO clones: 2.123-4 and 2.123-13 (Table 6). Cells in a volume of about 200 μl ($1 \times 10^6$ cells/ml) were transfected with 100 μg each of the heavy and light chain expression vectors, and 200 μl of Freestyle Max transfection reagent (Invitrogen). The conditioned media was harvested after cell viability reached below 70% in about 7 days and was subjected to Protein A chromatography to purify the antibody.

TABLE 6

| Transfection | Antibody | Host Cells | Fut8 |
|---|---|---|---|
| 2.191.2 | WT rituximab | WT CHOS | +/+ |
| 2.191.3 | AF rituximab | 2.123-4 | −/− |
| 5.3.2 | AF trastuzumab | 2.123-4 | −/ |
| 5.3.3 | AF trastuzumab | 2.123-13 | −/− |
| 5.9.1 | WT trastuzumab | WT CHOS | +/+ |

100 μg of wild-type (WT) or afucosylated (AF) antibodies were used for for glycan analysis. The purified antibodies were denatured and digested with trypsin. The N-glycans were subsequently enzymatically released from the peptides by treating with PNGase F, and then quantified with mass spectrometry. Each glycan was represented by a 5-digit code: number of hexose (Gal, Man, or Glc), number of N-acetylhexosamine (GlcNAc or GalNAc), number of deoxyhexose (Fuc), number of N-acetylneuraminic acid (Neu5Ac), and number of N-glycolylneuraminic acid (Neu5Gc). Fucose-containing glycans have 1 in the middle digit whereas glycans without fucose have 0 in the middle digit. For example, glycan 33100 contains 3 hexoses, 3 N-acetylhexosamines, and 1 fucose. Rituximab and trastuzumab produced from the wild-type CHOS cells exhibited robust fucose presence, whereas those antibodies produced from Fut8−/− CHO cells exhibited complete lack of fucose (FIG. 7).

The purified antibodies were also used to characterize ADCC activities. Human peripheral blood mononuclear cells (PBMC) were used as effectors. Human lymphoma Raji cells were used as target cells for rituximab whereas human breast cell line SK-BR3 were used as target cells for trastuzumab. The effector cells to target cells ratios were kept at 20:1. The cytotoxicity was determined by LDH release.

Figure 8A:
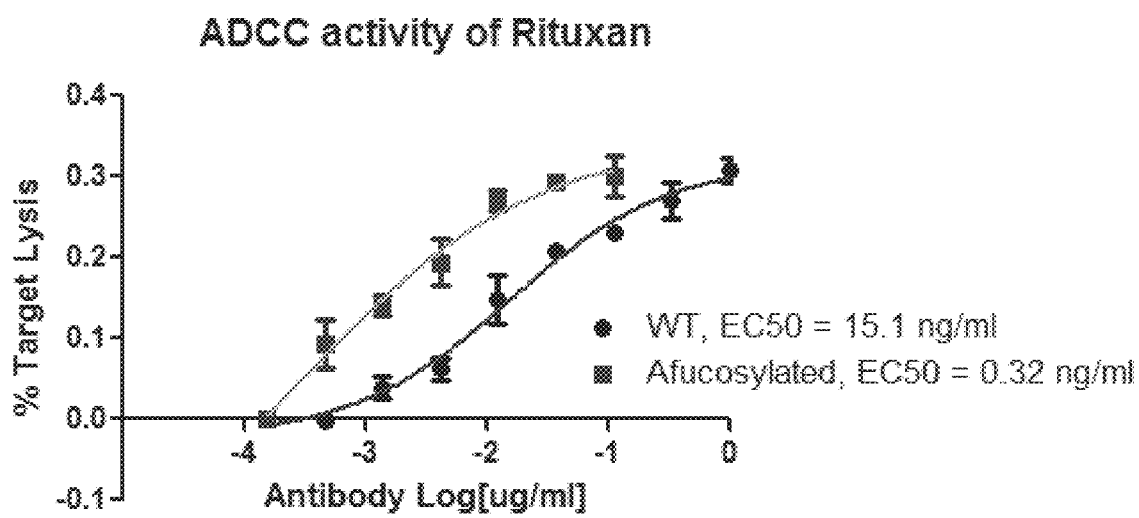
FIG. 8A-B shows antibody dependent cell cytotoxicity of rituximab (Rituxan) and trastuzumab (Herceptin) made in wild-type CHOS cells, and CHOS cells with double allele knock-outs of Fut8.
Figure 8B:
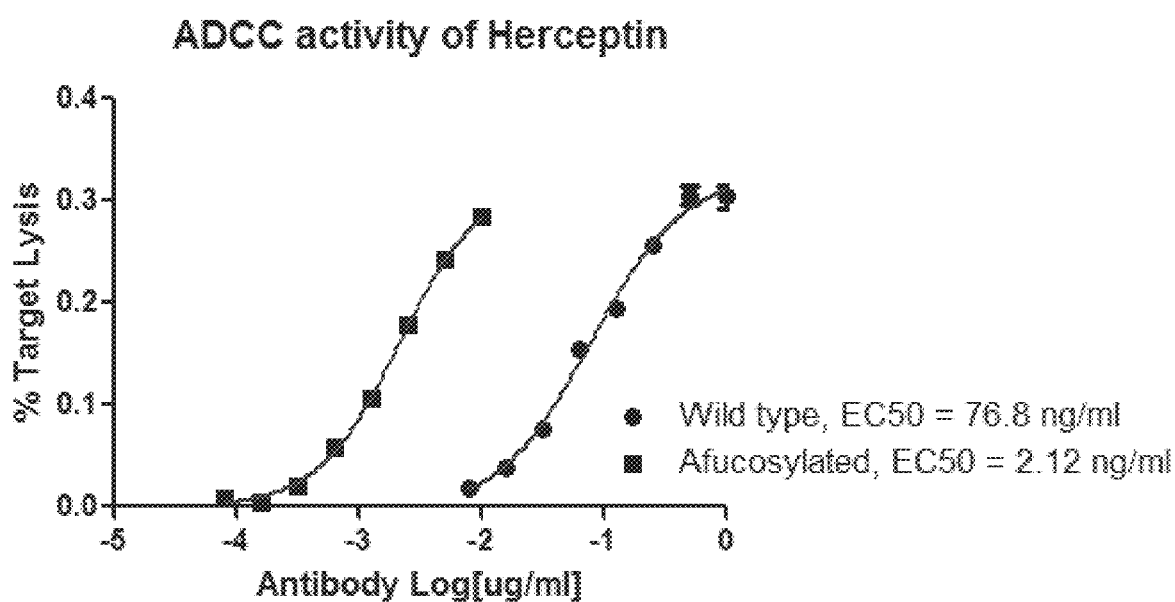

The target cells were washed and seeded in 96-well plates (10,000 cells in 50 µl). 50 µl of culture media with various concentrations of antibody was added to the cells and incubated for 30 min in cell culture incubator. The effector cells (200,000 cells in 100 µl, E:T=20:1) were then added to initiate the ADCC reaction. Final concentration of 1% of triton X-100 was added to control target cells without effector cells or antibody to lyse the target cells and served as the maximum lysis control. The assay buffers were added to control cells without effector cells or antibody and served as the minimum LDH release control. Target cells incubated with effector cells without the presence of antibodies were set as background control of non-specific LDH release. The 96-well plates were incubated at 37° C./5% $CO_2$ incubator for 6 hours. The ADCC activity was assayed with a LDH Cytotoxicity Assay Kit (Fisher Scientific). The afucosylated rituximab (FIG. 8a) and trastuzumab (FIG. 8b) exhibited ~50 and 40 fold, respectively, enhanced ADCC activities comparing to the wild-type antibody.

Example 5: Isolation of Fut8 Knock-Out Rituximab Production Cells

Biosimilar antibody rituximab heavy and light chain sequences were cloned into mammalian expression vectors under hEF1α promoter. After stable transfection in CHOS cells, a clone 2G8 was isolated that produced rituximab. $1 \times 10^6$ of the 2G8 cells were co-transfected with 5 µg each of vector LB200 and LB204 to knock out the Fut8 gene. One week after transfection, the cells were stained with fluorescence labeled LCA, and then subjected to flow cytometric analysis. The negative cells of LCA-FITC staining were sorted into single cells in 96-well plates. After colonies grew out in 2 weeks, the clones were expanded and confirmed for lack of LCA-FITC staining. Fut8 genes were sequenced and frame-shift mutations were confirmed.

Example 6: Disruption of Sialidase Genes in CHO Cells by Targeting Multiple crRNA Sites Sialylation influences pharmacokinetics, immunogenicity, and function of recombinant therapeutic glycoproteins (Bork, et al., *J Pharm Sci.*, 2009, 98: 3499-3508). The degree of sialylation correlates with serum half-life of recombinant proteins. Sialic acids are also important modulators of immunogenicity of recombinant proteins, a major problem with protein-based therapeutics. Sialic acids are important for masking antigenic determinants or epitopes. Thus, increased sialylation is generally preferred. Despite their influence on several important properties of recombinant proteins, sialic acid incorporation is highly variable. IgG and Fc fragments produced in CHO cells exhibit a very low level of sialylation (<2%; Raymond, 2012, Chapter 17, pp. 397-418. In: Biochemistry, Genetics and Molecular Biology, ed. S. Petrescu, InTech Open Access. ISBN 978-953-51-0771-2). Release of intracellular sialidases near the end of production culture is the main cause of low sialylation level.

The Chinese hamster genome contains 3 sialidase genes: lysosomal Neu1, cytoplasmic Neu2, and plasma membrane Neu3. Among them, Neu2 and Neu3 have been shown to affect sialylation levels of produced glycoproteins (Zhang and Ross, 2012, Compositions and methods for improved glycoprotein sialylation, U.S. Pat. No. 8,273,723). Particularly, Neu2 plays the most important role in removing sialic acid from the glycan after being released from dead cells at the end of batch culture production. Neu2 (GenBank: U06143.1) and Neu3 (GenBank: FJ476074.1) both contain 2 exons and open reading frames of 1137 and 1251 nt, encoding proteins of 379 and 417 amino acids, respectively.

Three CRISPR target protospacer sequences in Neu2 and Neu3 exons for genome editing in CHO cells are selected to minimize potential off-target modification as described (Hsu, P. D., et al., *Nat Biotechnol.*, 2013, 31:827-32). Expression vectors for CRISPR array, similar to the vector LB204, are constructed to contain 3 Neu2 protospacer targets or 3 Neu3 protospacer targets under the human U6 promoter.

We have previously optimized mammalian cell expression vector LB200 expressing Cas9 under the CMV promoter and tracrRNA under the human U6 promoter. We have also constructed LB221 (FIG. 2B) by inserting an IRES-EGFP cassette downstream of the Cas9 cDNA in the vector LB200 as a transfection reporter.

The CHO cells with be co-transfected with LB200 or LB221, and the vectors expressing CRISPR array targeting Neu2 and/or Neu3. If LB221 is used, the GFP-positive cells will be sorted into 96-well plates as single cells two days after transfection. After colonies grow out in 2-3 weeks, the plates will be duplicated into a new set of 96-well plates by passaging the cells 1:10. Triton X-100 (0.1%) or Tween 20 (0.5%) will be added to the original 96-well plates to permeabilize the cell membrane and release the cytoplasmic sialidase into the culture media. The clarified media will be used to assay sialidase activity with a fluorescent substrate methylumbelliferyl Neu5Ac (Neu5Ac-a-4MU, Santa Cruz Biotechnology). Media (100 uL) will be incubated with 4 mM Neu5Ac-a-4MU in black 96-well plates for 90 min. at 37° C. before addition of 100 µL of 0.2 M glycine buffer, pH 10.4, to stop the enzymatic reaction. The fluorescence will be measured using a plate reader with an excitation of 362 nm and an emission of 448 nm. The linear range of the assay will be determined. The change in fluorescence over the 90-min. incubation is directly proportional to the sialidase activities. All experiments will include wild-type CHO as a baseline control. Clones exhibiting less fluorescence in the assay likely contain Neu2 or Neu3 modification. The Neu2 and Neu3 sequences of these clones will be PCR-amplified and sequenced to confirm frameshift mutations. The sialidase negative clones will be expanded and cryopreserved. The Neu2 and Neu3 knock out maybe carried out sequentially or simultaneously.

All publications, patents, patent applications and other documents cited in this application are hereby incorporated by reference in their entireties for all purposes to the same extent as if each individual publication, patent, patent application or other document were individually indicated to be incorporated by reference for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of producing a double allele knock-out of a target gene in a eukaryotic cell, comprising the steps of: providing the cells with a CRISPR system comprising a Cas9 nuclease, wherein the Cas9 nuclease has two functional nuclease domains that produce a double-stranded break, and three to seven targeting RNAs located in the same gene, wherein each targeting RNA is comprised of a crRNA and a tracrRNA, wherein each crRNA has a different sequence, and expressing the CRISPR nuclease and the targeting RNAs whereby the target gene is knocked out in both alleles of the cell.

2. The method of claim 1, wherein the CRISPR system comprises three targeting RNAs.

3. The method of claim 2, wherein each targeting RNA has the same tracrRNA.

4. The method of claim 2, wherein at least two targeting RNAs are complementary to a corresponding target sequence in the targeted gene, and wherein the target sequences are located in a contiguous stretch of 375 bp, 200 bp, or 150 bp in the target gene.

5. The method of claim 1, wherein said cells are mammalian.

6. The method of claim 5, wherein said cells are CHO cells, 293 cells, NSO cells, embryonic stem cells, or derivatives thereof, or antibody-producing cells or derivatives thereof.

7. The method of claim 1, wherein the tracrRNA and the crRNA are connected by a hairpin RNA linkage.

8. The method of claim 1, wherein at least two targeting RNAs are complementary to a corresponding target sequence in the targeted gene, and wherein the target sequences are in a single exon of the targeted gene.

9. The method of claim 1, further comprising the step of providing the eukaryotic cells with a nucleic acid construct comprising a polynucleotide encoding an antibody and a control region operably linked to the polynucleotide encoding the polypeptide.

10. The method of claim 9, further comprising the step of expressing the antibody from the nucleic acid construct in the eukaryotic cell.

11. The method of claim 1, wherein the targeted gene is a fucosyltransferase.

12. The method of claim 1, wherein the targeted gene is glutamine synthetase.

13. The method of claim 1, wherein the targeted gene is dihydrofolate reductase (DHFR).

14. The method of claim 1, wherein the targeted gene is a sialidase.

15. The method of claim 1, further comprising the step of growing the eukaryotic cell that has the target gene knocked out in both alleles of the eukaryotic cell.

16. A method of producing a double allele knock-out of a target gene in a eukaryotic cell, comprising the steps of: providing the cells with a CRISPR system comprising a Cas9 nuclease, wherein the Cas9 nuclease has two functional nuclease domains that produce a double-stranded break, and three to seven targeting RNAs located in the same gene, wherein each targeting RNA is comprised of a crRNA and a tracrRNA, wherein each crRNA has a different sequence, expressing the CRISPR nuclease and the targeting RNAs whereby the target gene is knocked out in both alleles of the cell, and losing the CRISPR system from the eukaryotic cell.

17. The method of claim 16, further comprising the step of growing the eukaryotic cell that has the target gene knocked out in both alleles of the eukaryotic cell.

18. The method of claim 17, further comprising the step of providing the eukaryotic cells with a nucleic acid construct comprising a polynucleotide encoding an antibody and a control region operably linked to the polynucleotide encoding the polypeptide.

19. The method of claim 18, further comprising the step of expressing the antibody from the nucleic acid construct in the eukaryotic cell.

* * * * *